US010736948B2

(12) United States Patent
Charlton et al.

(10) Patent No.: US 10,736,948 B2
(45) Date of Patent: Aug. 11, 2020

(54) EPIDERMAL GROWTH FACTOR FUSION PROTEINS WITH MUTANT CHOLERA TOXIN B SUBUNITS

(71) Applicants: Keith Alan Charlton, Aberdeen (GB); Erik D'Hondt, Bazel (BE); Daniel T. Verhamme, Aberdeen (GB)

(72) Inventors: Keith Alan Charlton, Aberdeen (GB); Erik D'Hondt, Bazel (BE); Daniel T. Verhamme, Aberdeen (GB)

(73) Assignee: In3Bio Ltd., Hamilton (BM)

( * ) Notice: Subject to any disclaimer, the term of this patent is extended or adjusted under 35 U.S.C. 154(b) by 91 days.

(21) Appl. No.: 14/854,224

(22) Filed: Sep. 15, 2015

(65) Prior Publication Data

US 2016/0095910 A1    Apr. 7, 2016

Related U.S. Application Data

(63) Continuation-in-part of application No. PCT/IB2014/001125, filed on Mar. 17, 2014.

(60) Provisional application No. 61/791,268, filed on Mar. 15, 2013.

(51) Int. Cl.
| | |
|---|---|
| *A61K 39/00* | (2006.01) |
| *C07K 14/475* | (2006.01) |
| *C07K 14/485* | (2006.01) |
| *C07K 14/495* | (2006.01) |
| *C07K 14/50* | (2006.01) |

(52) U.S. Cl.
CPC ...... *A61K 39/0005* (2013.01); *A61K 39/0011* (2013.01); *C07K 14/475* (2013.01); *C07K 14/485* (2013.01); *C07K 14/495* (2013.01); *C07K 14/50* (2013.01); *C07K 2319/40* (2013.01)

(58) Field of Classification Search
None
See application file for complete search history.

(56) References Cited

U.S. PATENT DOCUMENTS

| | | | | |
|---|---|---|---|---|
| 5,894,018 A | * | 4/1999 | Davila | A61K 39/0005 424/130.1 |
| 7,320,795 B2 | * | 1/2008 | Milich | A61K 39/015 424/189.1 |
| 2006/0246087 A1 | | 11/2006 | Arakawa et al. | |
| 2008/0249019 A1 | * | 10/2008 | Foster | C07K 14/33 514/1.1 |

FOREIGN PATENT DOCUMENTS

| | | |
|---|---|---|
| JP | 2001507216 A | 6/2001 |
| JP | 2005052135 A | 3/2005 |
| JP | 2010207234 A | 9/2010 |
| JP | 2011045375 A | 3/2011 |
| JP | 2011097930 A | 5/2011 |
| RU | 2010137746 A | 3/2012 |
| WO | 98017799 A | 4/1998 |
| WO | 2001/027144 A2 | 4/2001 |
| WO | 03/000779 A1 | 1/2003 |
| WO | 030052064 A | 6/2003 |
| WO | 2005/056039 | 6/2005 |
| WO | 2005/077977 A2 | 8/2005 |
| WO | 2008058944 A1 | 5/2008 |
| WO | 2009/052628 A1 | 4/2009 |
| WO | 2009/078796 A1 | 6/2009 |
| WO | 2010080538 A1 | 7/2010 |
| WO | 2010050586 A1 | 3/2012 |
| WO | 2012/116453 A1 | 9/2012 |

OTHER PUBLICATIONS

Sequence alignment BLAST.Performed Oct. 29, 2019. (Year: 2019).*
Li S et al: "Pentabody-mediated antigen delivery induces antigen-specific mucosal immune response", Molecular Immunology, Pergamon, GB, vol. 46, No. 8-9, May 1, 2009 (May 1, 2009), pp. 1718-1726, XP026048427.
Hua Jiang et al: "Application of EGFP-EGF fusions to explore mechanism of endocytosis of epidermal growth factor", Acta Pharmacologica Sinica, Nature Publishing Group, US, CN.
Lebens M et al: "A mucosally administered recombinant fusion protein vaccine against schistosomiasis protecting against immunopathology and infection", Vaccine, Elsevier LTD, GB, vol. 21, No. 5-6, Jan. 17, 2003 (Jan. 17, 2003), pp. 514-520.
Boato Francesca et al: "Synthetic virus-like particles from self-assembling coiled-coil lipopeptides and their use in antigen display to the immune system", Angewandte Chemie International Edition, Wiley—V C H Verlag GMBH & Co. KGAA, DE, vol. 46, No. 47, Jan. 1, 2007 (Jan. 1, 2007), pp. 9015-9018.
Chain D, Cholera Toxin B-Pentamer Complexed with Gml Pentasaccharide, Genbank accession number:2CHB_D.

* cited by examiner

*Primary Examiner* — Elly-Gerald Stoica
(74) *Attorney, Agent, or Firm* — Burns & Levinson LLP; John C. Serio

(57) ABSTRACT

The present disclosure provides for a synthetic immunogenic protein for use as an immuno-modulatory agent to enhance mammalian immune reactions towards conjugated protein or peptide containing antigens that are otherwise poorly immunogenic, including but not limited to self-antigens. The chimeric immunogenic proteins of the present disclosure can be used in the treatment of many illnesses, including but not limited to cancers, infectious disease, autoimmune disease, allergies and any clinical indication involving or affected by the immune response of a mammalian host.

9 Claims, 13 Drawing Sheets
Specification includes a Sequence Listing.

Figure 1

| cut-off 0.025 | 1 | 2 | 3 | 4 | 5 | 6 | 7 | 8 | 9 | 10 | 11 | 12 | WT | WT (L7) med ctrl |
|---|---|---|---|---|---|---|---|---|---|---|---|---|---|---|
| A | 0 | 0 | 0 | 0 | 0 | 2.681 | 0 | 0 | 0 | 2.881 | 0.039 | 0.908 | | |
| B | 0 | 0 | 1.752 | 0 | 0 | 0.029 | 0 | 0 | 0 | 0 | 0 | 0.032 | | |
| C | 0 | 0 | 0 | 0 | 0 | 0 | 0 | 0 | 0 | 0 | 0 | 0 | | |
| D | 0 | 0 | 0 | 0 | 0 | 0 | 0 | 0 | 0 | 2.387 | 2.345 | 0.058 | | |
| E | 0 | 2.566 | 0 | 0 | 2.56 | 0 | 2.533 | 0 | 0.094 | 0 | 0 | 0 | | |
| F | 0 | 1.836 | 0 | 0 | 0 | 0 | 0 | 2.418 | 0 | 0 | 0.04 | 0.063 | | |
| G | 0.039 | 0 | 0 | 0.04 | 0 | 0 | 0 | 0 | 0.026 | 0 | 0.033 | 0.122 | | |
| H | 0 | 0 | 0 | 0 | 0 | 0 | 0 | 0 | 0.027 | 2.945 | 2.915 | 0.088 | | |

Figure 6

(SEQUENCE ID: 1)

FTDIITDICGEYHNTQIHTLNDKILSYTESLVGKREIILVNFKGGATFQVEVPGSQHIDSQKKAIERMK
DTLRIAYLSNSKIEKLCVWNNKTPHSIAAISMVR (SEQUENCE ID: 2)

ALDTNYCFSSTEKNCCVRQLYIDFRKDLGWKWIHEPKGYHANFCLGPCPYIWSLDTQYSKVLAL
YNQHNPGASAAPCCVPQALEPLPIVYYVGRKPKVEQLSNMIVRSCKCSGGSGGTSGGGGSG
FTDIITDICGEYHNTQIHTLNDKILSYTESLVGKREIILVNFKGGATFQVEVPGSQHIDSQKKAIERMK
DTLRIAYLSNSKIEKLCVWNNKTPHSIAAISMVR

Figure 12

IQDGITDLCAEYHNTQIHTLNDRIFSYTESLAGKREIILVNFKNGATFQVEVPGSFVSTLQAAAIERMKDTLRIA
YLTGAKVEKLCVWNNKTPHAIAAISMSG

Figure 13

IQDGITDLCAEYHNTQIHTLNDRIFSYTESLADKREIILVNFKNGATFQVEVPGSFVSTLQAAAIERMKDTLRDA
YLTGAKVEKLCVWNNKTPHAIAAISMSGSSGGSGGGSGPALPEDGGSGAFPPGHFKDPKRLYCKNGGFFLRI
HPDGRVDGVREKSDPHIKLQLQAEERGVVSIKGVCANRYLAMKEDGRLLASKCVTDECFFFERLESNNYNTY
RSRKYTSWYVALKRTGQYKLGSKTGPGQKAILFLPMSAKS

SEQUENCE LISTING

```
<160> NUMBER OF SEQ ID NOS: 18

<210> SEQ ID NO 1
<211> LENGTH: 101
<212> TYPE: PRT
<213> ORGANISM: Homo sapiens

<400> SEQUENCE: 1

Phe Thr Asp Ile Ile Thr Asp Ile Cys Gly Glu Tyr His Asn Thr Gln
1               5                   10                  15

Ile His Thr Leu Asn Asp Lys Ile Leu Ser Tyr Thr Glu Ser Leu Val
            20                  25                  30

Gly Lys Glu Ile Ile Leu Val Asn Phe Lys Gly Gly Ala Thr Phe Gln
        35                  40                  45

Val Glu Val Pro Gly Ser Gln His Ile Asp Ser Gln Lys Lys Ala Ile
    50                  55                  60

Glu Arg Met Lys Asp Thr Leu Arg Ile Ala Tyr Leu Ser Asn Ser Lys
65                  70                  75                  80

Ile Glu Lys Leu Cys Val Trp Asn Lys Thr Pro His Ser Ile Ala Ala
                85                  90                  95

Ile Ser Met Val Arg
            100

<210> SEQ ID NO 2
<211> LENGTH: 227
<212> TYPE: PRT
<213> ORGANISM: Homo sapiens

<400> SEQUENCE: 2

Ala Leu Asp Thr Tyr Cys Phe Ser Ser Thr Glu Lys Cys Cys Val Arg
1               5                   10                  15

Gln Leu Tyr Ile Asp Phe Arg Lys Asp Leu Gly Trp Lys Trp Ile His
            20                  25                  30

Glu Pro Lys Gly Tyr His Ala Asn Phe Cys Leu Gly Pro Cys Pro Tyr
        35                  40                  45

Ile Trp Ser Leu Asp Thr Gln Tyr Ser Lys Val Leu Ala Leu Tyr Asn
    50                  55                  60

Gln His Asn Pro Gly Ala Ser Ala Ala Pro Cys Cys Val Pro Gln Ala
```

```
                65                  70                  75                  80
Leu Glu Pro Leu Pro Ile Val Tyr Tyr Val Gly Arg Lys Pro Lys Val
                    85                  90                  95

Glu Gln Leu Ser Asn Met Ile Val Arg Ser Cys Lys Cys Ser Gly Gly
                100                 105                 110

Ser Gly Gly Thr Ser Gly Gly Gly Gly Ser Gly Phe Thr Asp Ile
        115                 120                 125

Ile Thr Asp Ile Cys Gly Glu Tyr His Asn Thr Gln Ile His Thr Leu
        130                 135                 140

Asn Asp Lys Ile Leu Ser Tyr Thr Glu Ser Leu Val Gly Lys Arg Glu
145                 150                 155                 160

Ile Ile Leu Val Asn Phe Lys Gly Gly Ala Thr Phe Gln Val Glu Val
                165                 170                 175

Pro Gly Ser Gln His Ile Asp Ser Gln Lys Lys Ala Ile Glu Arg Met
            180                 185                 190

Lys Asp Thr Leu Arg Ile Ala Tyr Leu Ser Asn Ser Lys Ile Glu Lys
                195                 200                 205

Leu Cys Val Trp Asn Asn Lys Thr Pro His Ser Ile Ala Ala Ile Ser
        210                 215                 220

Met Val Arg
225

<210> SEQ ID NO 3
<211> LENGTH: 103
<212> TYPE: PRT
<213> ORGANISM: Artificial Sequence
<220> FEATURE:
<223> OTHER INFORMATION: Construct

<400> SEQUENCE: 3

Ile Gln Asp Gly Ile Thr Asp Leu Cys Ala Glu Tyr His Asn Thr Gln
1               5                   10                  15

Ile His Thr Leu Asn Asp Arg Ile Phe Ser Tyr Thr Glu Ser Leu Ala
                20                  25                  30

Gly Lys Arg Glu Ile Ile Leu Val Asn Phe Lys Asn Gly Ala Thr Phe
            35                  40                  45

Gln Val Glu Val Pro Gly Ser Phe Val Ser Thr Leu Gln Ala Ala Ala
        50                  55                  60

Ile Glu Arg Met Lys Asp Thr Leu Arg Ile Ala Tyr Leu Thr Gly Ala
65                  70                  75                  80

Lys Val Glu Lys Leu Cys Val Trp Asn Asn Lys Thr Pro His Ala Ile
                85                  90                  95

Ala Ala Ile Ser Met Ser Gly
            100

<210> SEQ ID NO 4
<211> LENGTH: 259
<212> TYPE: PRT
<213> ORGANISM: Artificial Sequence
<220> FEATURE:
<223> OTHER INFORMATION: Construct

<400> SEQUENCE: 4

Ile Gln Asp Gly Ile Thr Asp Leu Cys Ala Glu Tyr His Asn Thr Gln
1               5                   10                  15

Ile His Thr Leu Asn Asp Arg Ile Phe Ser Tyr Thr Glu Ser Leu Ala
                20                  25                  30
```

```
Asp Lys Arg Glu Ile Ile Leu Val Asn Phe Lys Asn Gly Ala Thr Phe
            35                  40                  45

Gln Val Glu Val Pro Gly Ser Phe Val Ser Thr Leu Gln Ala Ala Ala
 50                  55                  60

Ile Glu Arg Met Lys Asp Thr Leu Arg Asp Ala Tyr Leu Thr Gly Ala
65                  70                  75                  80

Lys Val Glu Lys Leu Cys Val Trp Asn Asn Lys Thr Pro His Ala Ile
                85                  90                  95

Ala Ala Ile Ser Met Ser Gly Ser Gly Ser Gly Gly Ser
            100                 105                 110

Gly Pro Ala Leu Pro Glu Asp Gly Ser Gly Ala Phe Pro Pro Gly
            115                 120                 125

His Phe Lys Asp Pro Lys Arg Leu Tyr Cys Lys Asn Gly Gly Phe Phe
            130                 135                 140

Leu Arg Ile His Pro Asp Gly Arg Val Asp Gly Val Arg Glu Lys Ser
145                 150                 155                 160

Asp Pro His Ile Lys Leu Gln Leu Gln Ala Glu Glu Arg Gly Val Val
                165                 170                 175

Ser Ile Lys Gly Val Cys Ala Asn Arg Tyr Leu Ala Met Lys Glu Asp
            180                 185                 190

Gly Arg Leu Leu Ala Ser Lys Cys Val Thr Asp Glu Cys Phe Phe Phe
            195                 200                 205

Glu Arg Leu Glu Ser Asn Asn Tyr Asn Thr Tyr Arg Ser Arg Lys Tyr
            210                 215                 220

Thr Ser Trp Tyr Val Ala Leu Lys Arg Thr Gly Gln Tyr Lys Leu Gly
225                 230                 235                 240

Ser Lys Thr Gly Pro Gly Gln Lys Ala Ile Leu Phe Leu Pro Met Ser
                245                 250                 255

Ala Lys Ser

<210> SEQ ID NO 5
<211> LENGTH: 3
<212> TYPE: PRT
<213> ORGANISM: Artificial Sequence
<220> FEATURE:
<223> OTHER INFORMATION: Spacer

<400> SEQUENCE: 5

Ser Ser Gly
1

<210> SEQ ID NO 6
<211> LENGTH: 5
<212> TYPE: PRT
<213> ORGANISM: Artificial Sequence
<220> FEATURE:
<223> OTHER INFORMATION: Spacer

<400> SEQUENCE: 6

Ser Ser Gly Gly Gly
1               5

<210> SEQ ID NO 7
<211> LENGTH: 3
<212> TYPE: PRT
<213> ORGANISM: Artificial Sequence
<220> FEATURE:
<223> OTHER INFORMATION: Spacer

<400> SEQUENCE: 7
```

Ser Gly Gly
1

<210> SEQ ID NO 8
<211> LENGTH: 5
<212> TYPE: PRT
<213> ORGANISM: Artificial Sequence
<220> FEATURE:
<223> OTHER INFORMATION: Spacer

<400> SEQUENCE: 8

Gly Gly Ser Gly Gly
1               5

<210> SEQ ID NO 9
<211> LENGTH: 5
<212> TYPE: PRT
<213> ORGANISM: Artificial Sequence
<220> FEATURE:
<223> OTHER INFORMATION: Spacer

<400> SEQUENCE: 9

Gly Gly Gly Gly Ser
1               5

<210> SEQ ID NO 10
<211> LENGTH: 11
<212> TYPE: PRT
<213> ORGANISM: Artificial Sequence
<220> FEATURE:
<223> OTHER INFORMATION: Spacer

<400> SEQUENCE: 10

Ser Ser Gly Gly Gly Ser Gly Gly Ser Ser Gly
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Spacer

<400> SEQUENCE: 11

Gly Gly Ser Gly Gly Thr Ser Gly Gly Ser Gly
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Spacer

<400> SEQUENCE: 12

Ser Gly Gly Thr Ser Gly Gly Gly Gly Ser Gly Gly
1               5                   10

<210> SEQ ID NO 13
<211> LENGTH: 14
<212> TYPE: PRT
<213> ORGANISM: Artificial Sequence
<220> FEATURE:
<223> OTHER INFORMATION: Spacer

<400> SEQUENCE: 13

```
Gly Gly Ser Gly Gly Thr Ser Gly Gly Gly Ser Gly Gly
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Spacer

<400> SEQUENCE: 14

Ser Ser Gly Gly Gly Ser Gly Gly Ser Ser Gly
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Spacer

<400> SEQUENCE: 15

Ser Ser Gly Gly Gly Gly Ser Gly Gly Gly Ser Ser Gly
1               5                   10

<210> SEQ ID NO 16
<211> LENGTH: 13
<212> TYPE: PRT
<213> ORGANISM: Artificial Sequence
<220> FEATURE:
<223> OTHER INFORMATION: Spacer

<400> SEQUENCE: 16

Ser Ser Gly Gly Gly Ser Gly Gly Ser Ser Gly Gly Gly
1               5                   10

<210> SEQ ID NO 17
<211> LENGTH: 15
<212> TYPE: PRT
<213> ORGANISM: Artificial Sequence
<220> FEATURE:
<223> OTHER INFORMATION: Spacer

<400> SEQUENCE: 17

Ser Ser Gly Gly Gly Gly Ser Gly Gly Gly Ser Ser Gly Gly Gly
1               5                   10                  15

<210> SEQ ID NO 18
<211> LENGTH: 103
<212> TYPE: PRT
<213> ORGANISM: Vibrio cholerae

<400> SEQUENCE: 18

Thr Pro Gln Asn Ile Thr Asp Leu Cys Ala Glu Tyr His Asn Thr Gln
1               5                   10                  15

Ile His Thr Leu Asn Asp Lys Ile Phe Ser Tyr Thr Glu Ser Leu Ala
                20                  25                  30

Gly Lys Arg Glu Met Ala Ile Ile Thr Phe Lys Asn Gly Ala Thr Phe
            35                  40                  45

Gln Val Glu Val Pro Gly Ser Gln His Ile Asp Ser Gln Lys Lys Ala
        50                  55                  60

Ile Glu Arg Met Lys Asp Thr Leu Arg Ile Ala Tyr Leu Thr Glu Ala
65                  70                  75                  80
```

```
Lys Val Glu Lys Leu Cys Val Trp Asn Asn Lys Thr Pro His Ala Ile
            85                      90                  95
Ala Ala Ile Ser Met Ala Asn
            100
```

EPIDERMAL GROWTH FACTOR FUSION PROTEINS WITH MUTANT CHOLERA TOXIN B SUBUNITS

CROSS-REFERENCE TO RELATED APPLICATIONS

This application is a continuation-in-part of International Patent Application No. PCT/IB2014/001125, entitled SELF-ASSEMBLING SYNTHETIC PROTEINS, filed on Mar. 17, 2014, which in turn claims priority to U.S. Provisional Application No. 61/791,268 filed Mar. 15, 2013, which is incorporated by reference herein in its entirety.

FIELD OF THE INVENTION

The present invention relates to generation of a synthetic protein scaffold which exhibits specific functional and biophysical characteristics advantageous in the use of the synthetic protein to deliver and present antigens to the host immune system, even when said antigens are poorly or non-immunogenic in the host, such that the host is induced to raise a specific antibody response towards the antigens. A synthetic protein that is immunogenic to mammalian immune systems, and which can assemble into stable defined multimers is described. Further, a method for the use of said protein to confer immunogenicity and induce specific antibody responses to poorly or non-immunogenic peptides is described.

BACKGROUND OF THE INVENTION

The introduction of a foreign (non-self) substance, i.e. an antigen, to the immune system of a vertebrate usually results in the induction of an immune response by the host against that antigen. Typically this will involve the stimulation of B and/or T-lymphocytes, and the production of immunoglobulin molecules (antibodies) that recognise and bind to the antigen. There are a great many factors that influence the extent to which a substance will induce an immune response in a host. The degree of foreignness is important as the immune system has evolved and developed to be non-responsive to 'self'. Size is also a significant factor, with larger molecules generally being more immunogenic than smaller ones. Molecules below ~1000 Da molecular weight (classified as haptens) are too small to be seen by the immune system in isolation and are therefore non-immunogenic, though they may still be antigenic.

Larger molecules will be more complex and therefore more likely to contain multiple immunogenic epitopes, and are also more readily engulfed and processed by antigen presenting cells (APCs). The composition of the substance is also important, with proteins easily being the most immunogenic. Polysaccharides are much less immunogenic (in isolation) and nucleic acids and lipids are essentially non-immunogenic. Similarly, particulate or denatured antigens are more immunogenic than soluble and native molecules. The route of exposure and biological activities of foreign substances can also significantly affect the nature and extend of any immune response by the host. For example, parenteral injection of a substance that interacts with components or cells of the immune system will result in a much stronger response than mucosal exposure (ingestion/inhalation) of a relatively inert or inactive substance.

T-cells and B-cells recognise and respond to foreign antigens in different ways. Specialised antigen presenting cells or APC's (macrophages, dendritic cells and B-cells) continually interrogate their environment by taking up molecules from the extracellular space, including macro-molecules and whole micro-organisms, and processing the protein content of these. Exogenous proteins are digested by a panel of protease enzymes in endosomes, and the resulting peptides displayed on the surface of the cells in the groove of MHC II molecules. These in turn are recognised by specialist receptors on the surface of T-cells (TCRs). The process of T-cell development ensures that those T-cells displaying receptors that react to MHC II containing self-peptides are depleted, and only those that recognise foreign sequences mature successfully. The peptides recognised by T-cells (T-cell epitopes) are invariably linear, but are not always exposed or accessible on the native folded protein from which they were derived.

In contrast, the B-cell surface receptors or immunoglobulins (BCR) recognise and interact primarily with soluble proteins (both conformational and denatured epitopes), haptens, polysaccharides, and to a lesser extent some lipids and nucleic acids. The specificity of a BCR is identical to that of the antibody that the B-cell can secrete. Upon binding of its cognate antigen, the BCR is internalised and the bound antigen processed. Only when it is a protein, or is attached to a protein component, will it then be presented on the cell surface as part of an MHC II complex. Under these conditions, the B-cell is then available to be stimulated by a T-helper cell that has a TCR recognising the presented peptide. In the case of a large or complex protein, a B-cell can therefore be activated by a number of different T-cells, none of which need necessarily recognise the same antigenic epitope as the BCR, but all of which will recognise a peptide component of the same protein. It is this capacity of vertebrate immune systems that allows them to develop antibodies against antigenic determinants that are not in themselves immunogenic.

In order to develop effective vaccines, it is necessary to present antigenic epitopes to the host immune system in such a way as to stimulate a strong immune response, involving both T- and B-lymphocytes. Immune responses that do not involve activation of effector (helper) T-cells and subsequent stimulation of B-cells by these are usually short-lived and do not result in antigenic memory, i.e. do not lead to a more aggressive and more rapid antibody response when the host is exposed to the immunogen for a second time.

It is also often a requirement of vaccines to illicit antibodies that are able to inhibit, block or otherwise neutralize the functional activity of the target, and so afford protection to the host. This can present a major challenge for many reasons. Frequently, those epitopes that need to be targeted by an antibody response have not been identified due to a lack of structure-function data relating to the target. Even when detailed information relating to the target and its interactions, the identified epitope(s) may not be immuno-dominant and therefore might not generate the responses sought in the majority of patients. In other cases, the key protective antigenic determinants might not be protein, e.g. polysaccharides on pathogen glyco-proteins, and so not immunogenic (T-cell dependant) in isolation.

The vast majority of vaccines are delivered through parenteral routes; however there are many advantages to mucosal delivery such as patient compliance, self-administration, reduced risk of infection, and the possibility of inducing both mucosal and systemic immunity. There are also many obstacles to overcome, such as vaccine dilution, the presence of micro-flora, the need to withstand low pH when given orally, to cross membranes and the need for potent adjuvants (Vajdy et. al., 2004). Moreover, mucosal administration can lead to B-cell tolerance rather than an immune response. The dosage can also have a major effect on immune responses. If an immunogen is not effectively cleared by the immune system, or if the system is swamped by too high a dose, then tolerance can be induced. Conversely, too low a dose can also lead to tolerance, or simply fail to stimulate sufficient immune cells.

A number of approaches have been developed to help overcome these difficulties. In most cases, vaccines are administered along with some form of adjuvant. Adjuvants are essentially any formulation that, when administered together with an immunogen, causes one or more of persistence of the immunogen at the site of injection, enhancement of co-stimulatory signals, non-specific stimulation of lymphocyte proliferation or granuloma formation. They come in a variety of forms, for example Freund's complete adjuvant consists of inactivated Mycobacterium whilst others comprise an emulsion of oil (e.g. squalene) in water. These are most commonly used in animals as they can cause adverse reactions at the injection site. Some organic adjuvants are used in human vaccines such as Montanide© (mineral oil based with vegetable components) though more commonly they are inorganic such as aluminium salts.

Amongst the most popular and widely adopted methods to overcome low immunogenicity has been to couple an identified or desired antigen or antigenic determinant with a strongly immunogenic carrier. This is a protein or polypeptide derived from a different species, for example Bovine Serum Albumin (BSA) and Keyhole Limpet Hemocyanin (KLH) are often used as carriers of chemically conjugated haptens and small peptides to generate antibodies in animals (Berzofsky and Berzofsky 1993). The carrier presents the haptens on a molecule large enough to be seen and processed by the host immune system, and also stimulates the host immune response by being inherently immunogenic.

Generally speaking, carrier proteins derived from sources more phylogenically distant to the recipient are better. The carrier is then likely to be more different from host proteins and hence more foreign. A further important consideration when selecting a carrier protein is the possibility that if it is a homologue of a host protein, and so shares significant homology, then the elicited immune response might also react with host proteins and lead to adverse side effects. Non-protein antigens can only be coupled chemically, which may limit control over where on the carrier they are attached and how they are presented. Small peptides can be coupled chemically or genetically. In other areas of research, modern developments in bioinformatics have led to an increase in the rational design of immunogens, and in particular of peptides.

The concept of peptide vaccines is based on identification and chemical synthesis of B-cell and T-cell epitopes which are immunodominant and can induce specific immune responses, for example coupling a B-cell epitope of a target molecule to a widely recognised T-cell epitope to make it immunogenic (Naz R. K. and Dabir P. 2007). Peptides are seen as being relatively easy to produce when compared to larger and more complex protein antigens. They can also possess favourable chemical stability, and lack oncogenic or infectious potential making them attractive vaccine candidates. However, several obstacles limit the widespread usefulness of peptide vaccines including their often low inherent immunogenicity and the need for better adjuvants and carriers. Other research has suggested that recombinant chimeric proteins may be made more immunogenic if T helper epitopes are incorporated as tandem repeats (Kjerrulf M, et al. 1997).

Another popular class of carrier protein is bacterial toxoids. In the case of vaccines against bacterial infection where the symptoms of infection are caused by the action of toxins, then these can be used as the vaccine itself. It is of course necessary to render them inert, either chemically or by the use of a non-toxic component. Such attenuated toxins e.g. diphtheria and tetanus vaccines that were developed in the $20^{th}$ century are called toxoids. Polysaccharide-protein conjugate vaccines in use or late stage development by companies such as Wyeth (Pfizer), Aventis Pasteur, GSK, Merck and others use tetanus, diphtheria or other toxoids.

The B sub unit of Cholera toxin or *E. coli* heat labile enterotoxin (LT) have been proposed by many as a useful carrier proteins for various vaccine applications (Nemchinov, L. G et al. 2000, George-Chandy, A. et al. 2001, U.S. Pat. No. 6,153,203). It is highly immunogenic, and in the absence of the CT-A sub unit is non-toxic. Forming the basis of a widely used Cholera vaccine it has a demonstrated safety profile when used systemically. Whilst relatively small (~12 kDa), it can assemble into stable pentamers giving it a much higher molecular weight.

Of particular interest to many researchers is to exploit the affinity of CTB and enterotoxin pentamers to $G_{M1}$ ganglioside, a branched penta-saccharide found on the surface of nucleated cells. During cholera infection, it is this binding that facilitates the translocation of the holotoxin across the intestinal epithelium. There have been numerous reports in the literature that vaccines based on CTB fusions, chemical or genetic, can be effective at stimulating mucosal immunity (George-Chandy, A. et al. 2001, Houhui Song et al. 2003, Shenghua Li et al. 2009, Harakuni, A. et al. 2005) when administered orally or intra-nasally. In order to retain the ability to react with $G_{M1}$ ganglioside, which binds at the pocket formed between adjacent CTB subunits, it is essential that the target antigen does not block access to the $G_{M1}$ binding site and does not prevent the assembly of CTB multimers.

It has been demonstrated that genetic fusions can be made to CTB that successfully retain $G_{M1}$ binding, however there are also limitations. Liljeqvist, S. et al. (1997) showed that the serum albumin-binding domain of Strepococcal protein G could be fused genetically to either N- or C-terminus of CTB, or to both termini simultaneously, and retain $G_{M1}$ binding. It was noted however that the N-terminal fusion and the dual fusion proteins were significantly less efficient at forming stable pentamers, and less effective in binding to $G_{M1}$. Similarly, it has been demonstrated that large genetic fusions are unable to form pentamers unless a heterogenic mixture of both chimeric and wild type CTB are present (Harakuni, A. et al. 2005).

SUMMARY OF THE INVENTION

According to the disclosure, the highly immunogenic nature of a synthetic carrier is able to increase the host immune response to the included variable sequences due to its inherently immuno-stimulatory and adjuvant-like properties. It is further disclosed that the synthetic carrier according to the disclosure will cause the host to raise an antibody response to 'self' antigenic determinants encoded at least in part by the variable sequences.

In an illustrative embodiment, the recombinant synthetic protein is able to assemble into stable homo-pentamers, wherein each monomer includes one or more antigenic determinants derived from target proteins.

In another illustrative embodiment, the recombinant synthetic protein is able to assemble into stable hetero-pentamers, wherein monomers expressing different antigenic determinants are assembled together.

In a further illustrative embodiment, the recombinant synthetic protein is substantially similar to the following sequence:

(SEQ ID NO: 1)
FTDIITDICGEYHNTQIHTLNDKILSYTESLVGKREIILVNFKGGATFQV

EVPGSQHIDSQKKAIERMKDTLRIAYLSNSKIEKLCVWNNKTPHSIAAIS

MVR

In yet a further illustrative embodiment, the recombinant synthetic protein includes linker or spacer sequences, whereby the variable sequences positioned at one or both termini of the synthetic carrier are separated from the synthetic carrier in such a way as to enable the synthetic carrier elements from several recombinant proteins to associate. In one illustrative embodiment the recombinant synthetic protein having a linker sequence that attaches to a growth factor is substantially similar to the following sequence:

(SEQ ID NO: 2)
ALDTNYCFSSTEKNCCVRQLYIDFRKDLGWKWIHEPKGYHANFCL

GPCPYIWSLDTQYSKVLALYNQHNPGASAAPCCVPQALEPLPIVYYVGRK

PKVEQLSNMIVRSCKCSGGSGGTSGGGGSGFTDIITDICGEYHNTQIHT

LNDKILSYTESLVGKREIILVNFKGGATFQVEVPGSQHIDSQKKAIERMK

DTLRIAYLSNSKIEKLCVWNNKTPHSIAAISMVR

In another illustrative embodiment the recombinant synthetic protein will associate into stable pentamers in the form of a ring. Other multimeric assemblies, for example but not limited to dimers, trimers, tetramers and larger multimers are also envisaged within the scope of the disclosure. The linker sequences can be varied, and as a minimum should be of sufficient length to prevent the variable antigenic determinant sequences from sterically inhibiting assembly of multimers by association of synthetic carrier domains. It is contemplated within the scope of the disclosure that the linkers or spacers can be flexible allowing for the formative of stable pentamers.

In another embodiment, the pentameric structure of the multimer is stabilized by the introduction of at least one stabilizing molecule. The stabilizing molecule can be co-expressed in the same cells as the synthetic molecule, or alternatively can be added exogenously.

In one embodiment, the stabilizing molecule includes sequences substantially similar to the CT-A2 domain of cholera toxin.

In another embodiment, the stabilizing molecule comprises sequences that interact with the synthetic protein such as to stabilise the multimers. It is further contemplated that this stabilization may result in a greater proportion of pentameric forms using recognized manufacturing techniques known in the art.

In a further illustrative embodiment, the stabilizing molecule can serve to anchor an antigenic domain to the multimeric form of the synthetic protein.

In yet a further embodiment, interrupted repeats of the stabilizing molecule can serve to associate two or more multimeric forms of the synthetic protein.

In an illustrative embodiment, the linkers or spacers sequences will be generally hydrophilic, and be flexible such that they include no defined secondary structure.

In another illustrative embodiment, the linker sequences will such that they do not directly or indirectly influence the folding of the synthetic carrier domain, or of the variable antigenic determinant domains.

In a further illustrative embodiment, the linker sequences will be resistant to proteolysis by extracellular proteases.

In another illustrative embodiment, the linker or spacer sequences include but are not limited to the following: SSG (SEQ ID NO:5), SSGGG (SEQ ID NO:6), SGG (SEQ ID NO:7), GGSGG (SEQ ID NO:8), GGGGS (SEQ ID NO:9), SSGGGSGGSSG (SEQ ID NO:10), GGSGGTSGGGSG (SEQ ID NO:11), SGGTSGGGGSGG (SEQ ID NO:12), GGSGGTSGGGGSGG (SEQ ID NO:13), SSGGGSGGSSG (SEQ ID NO:14), SSGGGGSGGGSSG (SEQ ID NO:15), SSGGGSGGSSGGG (SEQ ID NO:16), and SSGGGGSGGGSSGGG (SEQ ID NO:17).

In one illustrative embodiment, the linker sequences will include sequences that, either alone or in conjunction with flanking sequences from the variable antigenic determinants or synthetic carrier, will form T-cell epitopes. Preferably, the T-cell epitopes will be T-cell epitopes as recognised by human T-helper cells when bound by MHC (Major Histocompatibility Complex) class II proteins. Preferably, the T-cell epitopes will be bound by MHC II molecules of the HLA (human leukocyte antigen)-DR sub-class.

In another illustrative embodiment the synthetic recombinant protein is structurally homologous to B-sub unit of the A1B5 group of bacterial holotoxins.

In a further illustrative embodiment, multimers of the recombinant synthetic protein are able to bind to $G_{M1}$ ganglioside.

In an illustrative embodiment, the synthetic recombinant protein is an immunogenic protein that induces an immune response in mammalian hosts.

In another illustrative embodiment, the synthetic recombinant protein is an immunogenic protein including one or more variable sequences that represent antigenic determinants to which it is desirable to generate an immune response by patients. The variable sequences can be located at the N- and/or C-terminus of the sequence encoding the synthetic carrier, or can be incorporated within the synthetic carrier encoding sequence such that they are presented appropriately to the cells of the immune system. In a preferred embodiment the variable sequences are presented in such a way as to replicate the conformation that the sequences display in the natural molecules from which they are derived, and are accessible to the immunoglobulin cell-surface receptors of B-cells.

In another illustrative embodiment, the variable antigenic determinants are derived from signalling molecules, including but not limited to growth factors such as adrenomedullin (AM), angiopoietin (Ang), bone morphogenetic proteins, epidermal growth factor (EGF), fibroblast growth factor (FGF), hepatocyte growth factor (HGF), insulin-like growth factor (IGF), nerve growth factor (NGF) and other neurotrophins, platelet-derived growth factor (PDGF), transforming growth factor alpha(TGF-α), transforming growth factor beta(TGF-β), tumor_necrosis_factor-alpha(TNF-α) and vascular endothelial growth factor (VEGF).

In another embodiment, the variable antigenic determinants are derived from other ligand molecules involved in the development or progression of disease, such as, but not limited to PDL1.

In another embodiment, the variable antigenic determinants are derived from receptors found on the surface of cells, and involved in signaling events that regulate the growth of cells such as the natural receptors of growth factors.

In a further embodiment, the variable antigenic determinants are derived from tumor antigens.

In yet another embodiment, the variable antigenic determinants are derived from bacterial, viral, fungal or other pathogens.

BRIEF DESCRIPTION OF DRAWINGS

The embodiments described in the present disclosure are illustrated in the figures of the accompanying drawings which are meant to be exemplary and not limiting, in which like references are intended to refer to like or corresponding parts, and in which:

FIG. 1. Illustrates the ELISA signals produced by a panel of soluble mutant clones binding to an immobilized galactose-containing molecule (GM1), following 3 rounds of selection;

FIG. 6. Illustrates sequences of the synthetic protein according to the disclosure (SEQ ID NO: 1); and a further sequence of synthetic protein according to the disclosure comprising sequences encoding human TGF Beta1 (Bold), a flexible linker (Italicized), and synthetic protein carrier (SEQ ID NO: 2);

FIG. 12. Illustrates sequences of the synthetic protein according to the disclosure comprising amino acid sequence (SEQ ID NO: 3) of synthetic carrier protein indicated are glycine-33 and isoleucine-74 (bold and underlined), resulting in absence of GM1-binding and assembly with CTA, respectively, when changed to an aspartate (G33D and I74D in SEQ ID NO: 4); and FIG. 13. Illustrates a further sequence of synthetic protein according to the disclosure (SEQ ID NO: 4) comprising amino acid sequence of synthetic protein comprising sequences encoding synthetic carrier, a flexible linker (in italics), and human growth factor FGF2 (underlined).

DETAILED DESCRIPTION

Figure 2:
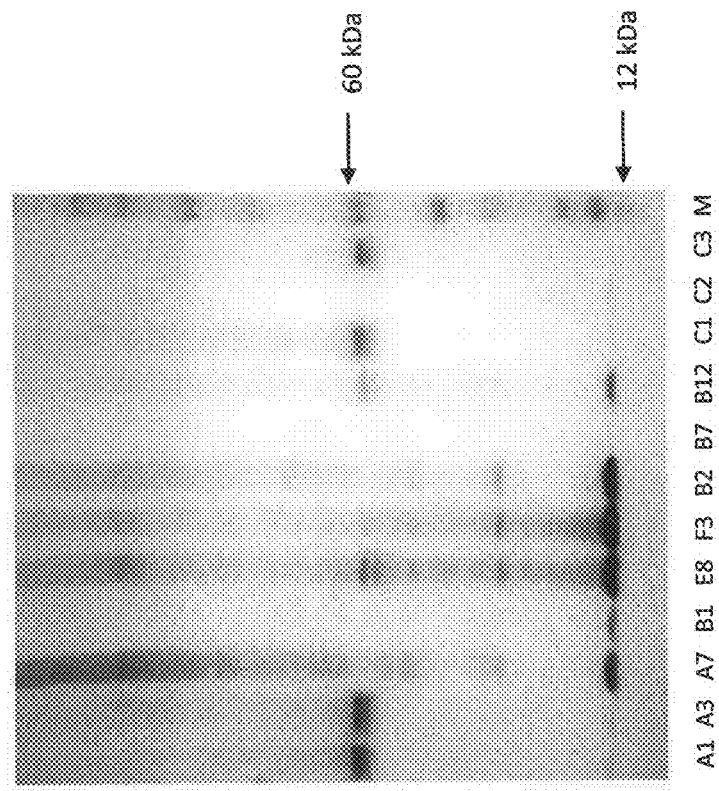
FIG. 2. Illustrates a Western blot of soluble mutant proteins from one of the mutant libraries electrophoresed on an SDS gel, some of which retain the ability to form pentamers, and others that do not.

Detailed embodiments of the present recombinant proteins or vaccines are disclosed herein, however, it is to be understood that the disclosed embodiments are merely exemplary, which may be embodied in various forms. Therefore, specific functional details disclosed herein are not to be interpreted as limiting, but merely as a basis for the claims and as a representative basis for teaching one skilled in the art to variously employ the recombinant protein disclosed herein.

The present disclosure provides a synthetic recombinant protein for improving the presentation of the maximum number of growth factor epitopes, tumor antigen epitopes, and/or receptor binding sites as elements of an immunogenic recombinant protein.

In one illustrative embodiment, a synthetic recombinant protein as shown in SEQ ID NO: 2 containing at least one growth factor including but not limited to human transforming growth factor (TGF), a tumor antigen, and/or a receptor is described. In alternative illustrative embodiments, the protein may express other immunogenic recombinant proteins that are modeled based upon known immunogenic proteins. It is contemplated within the scope of the disclosure that such recombinant proteins will be expressions of polypeptides that are highly immunogenic to the human immune system. Preferably, the recombinant proteins confer additional properties to the chimeric protein, for example, high expression yield and ease of manufacture, oral stability and the ability to cross from gut to blood stream, and/or previous safe use in humans.

Certain illustrative embodiments as provided herein include recombinant proteins according to the disclosure within vaccine compositions and immunological adjuvant compositions, including pharmaceutical compositions, that contain, in addition to recombinant proteins at least one adjuvant, which refers to a component of such compositions that has adjuvant activity.

An adjuvant having such adjuvant activity includes a composition that, when administered to a subject such as a human (e.g., a human patient), a non-human primate, a mammal or another higher eukaryotic organism having a recognized immune system, is capable of altering (i.e., increasing or decreasing in a statistically significant manner, and in certain preferred embodiments, enhancing or increasing) the potency and/or longevity of an immune response. In certain illustrative embodiments disclosed herein a desired antigen and or antigens contain within a protein carrier, and optionally one or more adjuvants, may so alter, e.g., elicit or enhance, an immune response that is directed against the desired antigen and or antigens which may be administered at the same time or may be separated in time and/or space (e.g., at a different anatomic site) in its administration, but certain illustrative embodiments are not intended to be so limited and thus also contemplate administration of recombinant protein in a composition that does not include a specified antigen but which may also include but is not limited to one or more co-adjuvant, an imidazoquinline immune response modifier.

Accordingly and as noted above, adjuvants include compositions that have adjuvant effects, such as saponins and saponin mimetics, including QS21 and QS21 mimetics (see, e.g., U.S. Pat. No. 5,057,540; EP 0 362 279 B1; WO95/17210), alum, plant alkaloids such as tomatine, detergents such as (but not limited to) saponin, polysorbate 80, Span 85 and stearyl tyrosine, one or more cytokines (e.g., GM-CSF, IL-2, IL-7, IL-12, TNF-alpha, IFN-gamma), an imidazoquinoline immune response modifier, and a double stem loop immune modifier (dSLIM, e.g., Weeratna et al., 2005 Vaccine 23:5263).

Detergents including saponins are taught in, e.g., U.S. Pat. No. 6,544,518; Lacaille-Dubois, M and Wagner H. (1996 Phytomedicine 2:363-386), U.S. Pat. No. 5,057,540, Kensil, Crit. Rev Ther Drug Carrier Syst, 1996, 12 (1-2):1-55, and EP 0 362 279 B1. Particulate structures, termed Immune Stimulating Complexes (ISCOMS), comprising fractions of Quil A (saponin) are haemolytic and have been used in the manufacture of vaccines (Morein, B., EP 0 109 942 B1). These structures have been reported to have adjuvant activity (EP 0 109 942 B1; WO 96/11711). The haemolytic saponins QS21 and QS17 (HPLC purified fractions of Quil A) have been described as potent systemic adjuvants, and the method of their production is disclosed in U.S. Pat. No. 5,057,540 and EP 0 362 279 B1. Also described in these references is the use of QS7 (a non-haemolytic fraction of Quil-A) which acts as a potent adjuvant for systemic vaccines. Use of QS21 is further described in Kensil et al. (1991. J. Immunology 146:431-437). Combinations of Q S21 and polysorbate or cyclodextrin are also known (WO 99/10008). Particulate adjuvant systems comprising fractions of QuilA, such as QS21 and QS7 are described in WO 96/33739 and WO 96/11711. Other saponins which have been used in systemic vaccination studies include those derived from other plant species such as *Gypsophila* and *Saponaria* (Bomford et al., Vaccine, 10 (9):572-577, 1992).

[0203] Escin is another detergent related to the saponins for use in the adjuvant compositions of the embodiments herein disclosed. Escin is described in the Merck Index (12.sup.th Ed.: entry 3737) as a mixture of saponin occurring in the seed of the horse chestnut tree, Aesculus hippocastanum. Its isolation is described by chromatography and purification (Fiedler, Arzneimittel-Forsch. 4, 213 (1953)), and by ion-exchange resins (Erbring et al., U.S. Pat. No. 3,238,190). Fractions of escin (also known as aescin) have been purified and shown to be biologically active (Yoshikawa M, et al. (Chem Pharm Bull (Tokyo) 1996 August; 44(8):1454-1464)). Digitonin is another detergent, also being described in the Merck index (12th Ed., entry 3204) as a saponin, being derived from the seeds of *Digitalis purpurea* and purified according to the procedure described by Gisvold et al., J. Am. Pharm. Assoc., 1934, 23, 664; and Rubenstroth-Bauer, Physiol. Chem., 1955, 301, 621.

Other adjuvants or co-adjuvants for use according to certain herein disclosed embodiments include a block co-polymer or biodegradable polymer, which refers to a class of polymeric compounds with which those in the relevant art will be familiar. Examples of a block co-polymer or biodegradable polymer that may be included in a vaccine composition or an immunological adjuvant include Pluronic® L121 (BASF Corp., Mount Olive, N.J.; see, e.g., Yeh et al., 1996 Pharm. Res. 13:1693), Certain further illustrative embodiments contemplate immunological adjuvants that include but are not limited to an oil, which in some such embodiments may contribute co-adjuvant activity and in other such embodiments may additionally or alternatively provide a pharmaceutically acceptable carrier or excipient. Any number of suitable oils are known and may be selected for inclusion in vaccine compositions and immunological adjuvant compositions based on the present disclosure. Examples of such oils, by way of illustration and not limitation, include squalene, squalane, mineral oil, olive oil, cholesterol, and a mannide mono-oleate.

Immune response modifiers such as imidazoquinoline are also known in the art and may also be included as adjuvants or coadjuvants in certain presently disclosed embodiments. As also noted above, one type of adjuvant or co-adjuvant for use in a vaccine composition according to the disclosure as described herein may be the aluminium co-adjuvants, which are generally referred to as "alum." Alum co-adjuvants are based on the following: aluminium oxy-hydroxide; aluminium hydroxyphosphoate; or various proprietary salts. Alum co-adjuvants are be advantageous because they have a good safety record, augment antibody responses, stabilize antigens, and are relatively simple for large-scale production. (Edelman 2002 Mol. Biotechnol. 21:129-148; Edelman, R. 1980 Rev. Infect. Dis. 2:370-383.)

Pharmaceutical Compositions

In certain illustrative embodiments, the pharmaceutical composition is a vaccine composition that comprises both the recombinant protein according to the disclosure and may further comprise one or more components, as provided herein, that are selected from TLR agonist, co-adjuvant (including, e.g., a cytokine, an imidazoquinoline immune response modifier and/or a dSLIM) and the like and/or a recombinant expression construct, in combination with a pharmaceutically acceptable carrier, excipient or diluent.

Illustrative carriers will be nontoxic to recipients at the dosages and concentrations employed. For vaccines comprising recombinant protein, about 0.01 mu·g/kg to about 100 mg/kg body weight will be administered, typically by the intradermal, subcutaneous, intramuscular or intravenous route, or by other routes. It will be evident to those skilled in the art that the number and frequency of administration will be dependent upon the response of the host. "Pharmaceutically acceptable carriers" for therapeutic use are well known in the pharmaceutical art, and are described, for example, in Remington's Pharmaceutical Sciences, Mack Publishing Co. (A. R. Gennaro edit. 1985). For example, sterile saline and phosphate-buffered saline at physiological pH may be used. Preservatives, stabilizers, dyes and even flavouring agents may be provided in the pharmaceutical composition. For example, sodium benzoate, ascorbic acid and esters of p-hydroxybenzoic acid may be added as preservatives. In addition, antioxidants and suspending agents may be used.

The pharmaceutical compositions may be in any form which allows for the composition to be administered to a patient. For example, the composition may be in the form of a solid, liquid or gas (aerosol). Typical routes of administration include, without limitation, oral, topical, parenteral (e.g., sublingually or buccally), sublingual, rectal, vaginal, and intranasal (e.g., as a spray). The term parenteral as used herein includes iontophoretic, sonophoretic, passive transdermal, micro-needle administration and also subcutaneous injections, intravenous, intramuscular, intrasternal, intracavernous, intrathecal, intrameatal, intraurethral injection or infusion techniques. In a particular embodiment, a composition as described herein (including vaccine and pharmaceutical compositions) is administered intradermally by a technique selected from iontophoresis, micro-cavitation, sonophoresis or micro-needles.

The pharmaceutical composition is formulated so as to allow the active ingredients contained therein to be bioavailable upon administration of the composition to a patient. Compositions that will be administered to a patient take the form of one or more dosage units, where for example, a tablet may be a single dosage unit, and a container of one or more compounds of the invention in aerosol form may hold a plurality of dosage units.

For oral administration, an excipient and/or binder may be present. Examples are sucrose, kaolin, glycerin, starch dextrins, sodium alginate, carboxymethylcellulose and ethyl cellulose. Coloring and/or flavoring agents may be present. A coating shell may be employed.

The composition may be in the form of a liquid, e.g., an elixir, syrup, solution, emulsion or suspension. The liquid may be for oral administration or for delivery by injection, as two examples. When intended for oral administration, preferred compositions contain one or more of a sweetening agent, preservatives, dye/colorant and flavour enhancer. In a composition intended to be administered by injection, one or more of a surfactant, preservative, wetting agent, dispersing agent, suspending agent, buffer, stabilizer and isotonic agent may be included.

A liquid pharmaceutical composition as used herein, whether in the form of a solution, suspension or other like form, may include one or more of the following carriers or excipients: sterile diluents such as water for injection, saline solution, preferably physiological saline, Ringer's solution, isotonic sodium chloride, fixed oils such as squalene, squalane, mineral oil, a mannide monooleate, cholesterol, and/or synthetic mono or digylcerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. An injectable pharmaceutical composition is preferably sterile.

In a particular embodiment, a pharmaceutical or vaccine composition of the invention comprises a stable aqueous suspension of less than 0.2 um and further comprises at least one component selected from the group consisting of phospholipids, fatty acids, surfactants, detergents, saponins, fluorodated lipids, and the like.

It may also be desirable to include other components in a vaccine or pharmaceutical composition, such as delivery vehicles including but not limited to aluminium salts, water-in-oil emulsions, biodegradable oil vehicles, oil-in-water emulsions, biodegradable microcapsules, and liposomes. Examples of additional immunostimulatory substances (co-adjuvants) for use in such vehicles are also described above and may include N-acetylmuramyl-L-alanine-D-isoglutamine (MDP), glucan, IL-12, GM-CSF, gamma interferon and IL-12.

While any suitable carrier known to those of ordinary skill in the art may be employed in the pharmaceutical compositions of this invention, the type of carrier will vary depending on the mode of administration and whether a sustained release is desired. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention.

Pharmaceutical compositions may also contain diluents such as buffers, antioxidants such as ascorbic acid, low molecular weight (less than about 10 residues) polypeptides, proteins, amino acids, carbohydrates, including glucose, sucrose or dextrins, chelating agents such as EDTA, glutathione and other stabilizers and excipients. Neutral buffered saline or saline mixed with nonspecific serum albumin are exemplary appropriate diluents. Preferably, product may be formulated as a lyophilizate using appropriate excipient solutions (e.g., sucrose) as diluents.

In an illustrative embodiment, the epitope or receptor supporting domain of the recombinant protein, whether derived from a natural or synthetic polypeptide sequence, should have the capacity to self-assemble into oligomeric multimers under appropriate chemical/environmental conditions, or to be reduced to monomers under alternative conditions. Ideally, multimerization domains will assemble into stable multimers with a discreet number of sub-units, for example dimers, trimers, tetramers, pentamers, etc., such that a product of homogeneous size is generated. Without being bound to any particular theory, it is thought that the recombinant synthetic protein, as set forth in SEQ ID NO: 1, will allow assembly into stable multimers with an insignificant number of sub-units. Examples of natural polypeptides include, but are not limited to, leucine zippers, lac repressor protein, streptavidin/avidin, cholera toxin B subunit, *Pseudomonas* trimerization domain, and viral capsid proteins.

According to the disclosure, the recombinant proteins, whether growth factors or parts thereof, cellular receptors or parts thereof, tumor antigens or parts thereof, are related to broad range of either cellular pathways involved in chronic disease or cancers for growth factors and receptors and to broadest possible range of solid tumors for use of tumor antigens within the said synthetic proteins. The proteins are in the form of a recombinant protein and may be useful in treating chronic diseases, for example, breast, lung, bladder, ovarian, vulva, colonic, pulmonary, brain, colorectal, intestinal, head and neck, and esophageal cancers. As different tumor antigens can be expressed and multiple cellular receptors and growth factors over expressed in the said diseases, the proteins described hereunder can contain one or more different tumor antigens, one or more different receptors or growth factors of one or multiple cellular pathways associated with the disease. These proteins are called "multivalent."

In the context of the present disclosure, "neutralizing domain" is defined as a region or regions of either or both member(s) of a specific binding pair, e.g. a growth factor and its cognate receptor, wherein the binding of a third molecule that is not a member of the specific binding pair to the aforementioned region(s) will prevent the subsequent binding of the two members of the specific binding pair. The third molecule can be another protein molecule including but not limited to an antibody, or can be a small non-protein molecule, and can be either natural or synthetic in origin.

The neutralizing domain will normally include those regions of the members of the specific binding pair that are in direct contact during binding, and will also include regions outwith said regions where upon binding of a third molecule introduces sufficient stearic hindrance to prevent the members of the specific binding pair from binding directly.

It is well established in the field that specific recognition of a ligand by its cognate receptor is defined by an interaction between the binding site of the receptor and a particular molecular signature (epitope) of the ligand. Thus an antibody that either binds to or otherwise blocks the receptor binding site, or binds to or otherwise blocks the recognition epitope of the ligand, will prevent ligand receptor interactions. Such antibodies are described as being "neutralizing." In the context of the present disclosure it is desirable that neutralizing antibodies are generated by the host upon administration of the recombinant protein, and thus the protein sequence may express or include one or more of all of, or a suitable sequence derived from, a growth factor or tumor antigen such that epitopes required for receptor binding are presented in a functional (native) conformation.

In addition to expressing multiple copies of a single tumor antigen, receptor, and/or growth factor, presented as a single tumor antigen, receptor, and/or growth factor or part thereof per physical site, and/or as chains of repetitive tumor antigen, receptor, and/or growth factor sequences (for example, n=1 or more); the protein according to the disclosure may also include expressions of one or more epitopes or binding sites from two or more different tumor antigens, receptors, and/or growth factors present as single or as chains at different positions within the sequence of the recombinant protein.

In an illustrative embodiment, a protein comprised of a homogeneous recombinant protein expressing one or more epidermal growth factor (EGF) neutralizing domains is disclosed. The protein is in the form of a recombinant protein and may be useful in treating chronic diseases, for example, breast, lung, bladder, ovarian, vulva, colonic, pulmonary, brain, colorectal, head and neck, and esophagus cancers. In an illustrative embodiment, the protein is a recombinant protein expressing or including EGF sequences and synthetic polypeptide sequences according to the disclosure. In one illustrative embodiment the synthetic polypeptide sequence is substantially similar to SEQ ID NO: 1.

In another illustrative embodiment, a protein comprised of a homogeneous recombinant protein expressing one fibroblast growth factor (FGF) is disclosed.

In a further illustrative embodiment, the protein is a recombinant protein expressing or including FGF sequences and synthetic polypeptide sequences according to the disclosure.

In yet a further illustrative embodiment, a protein comprised of a homogeneous recombinant protein expressing one transforming growth factor Beta 1 (TGF-β1) is disclosed. In an illustrative embodiment, the protein is a recombinant protein expressing or including TGF-β1 sequences and synthetic polypeptide sequences according to the disclosure.

In yet another illustrative embodiment, a protein comprised of a homogeneous recombinant protein expressing one transforming growth factor-Beta 1 (TGF-β1) is disclosed. In an illustrative embodiment, the protein is a recombinant protein expressing or including TGF-β1 sequences and synthetic polypeptide sequences substantially similar to SEQ ID NO: 2 according to the disclosure.

In another illustrative embodiment, expressing one insulin-like growth factor-1 (IGF-1) is disclosed. In an illustrative embodiment, the protein is a recombinant protein expressing or including IGF-1 sequences and synthetic polypeptide sequences a protein comprised of a homogeneous recombinant protein expressing one hepatocyte growth factor (HGF) is disclosed.

In a further illustrative embodiment, the protein is a recombinant protein expressing or including HGF sequences and synthetic polypeptide sequences according to the disclosure.

In a further illustrative embodiment, a protein comprised of a homogeneous recombinant protein expressing one Insulin-like growth factor-1 (IGF-1) and one insulin-like growth factor-2 is disclosed. In an illustrative embodiment, the protein is a recombinant protein expressing or including IGF-1 sequences, IGF-2 sequences and synthetic polypeptide sequences according to the disclosure.

In yet another illustrative embodiment, a protein comprised of a homogeneous recombinant protein expressing one vascular endothelial growth factor-A (VEGF-A) and one vascular endothelial growth factor-C (VEGF-C) is disclosed. In an illustrative embodiment, the protein is a recombinant protein expressing or including VEGF-A neutralizing domain sequences, VEGF-C sequences and synthetic polypeptide sequences according to the disclosure.

EXAMPLES

Aspects of the disclosure are further described in detail as in the following examples. However, the following examples are not intended to limit the scope of the disclosure to the precise details of methodology or construction set forth below. Practical and illustrative embodiments are illustrated and described in the following examples. However, it will be appreciated that those skilled in the art may make modifications and improvements within the spirit and scope of the present disclosure.

Example 1

Construction of a Selectable Carbohydrate-Binding Display System

A system whereby libraries of mutants could be generated and screened for mutants with desirable characteristics was needed that included a physical linkage between the selectable phenotype and the encoding genotype of a diverse population of clones. Such a system was developed using established technologies employed to great effect in the field of antibody engineering amongst others.

A gene encoding the chosen carbohydrate-binding domain was cloned in-frame and upstream of the minor coat protein gene (gene III) of M13 bacteriophage, in both a complete independently functional M13 'phage' vector with a suitable selectable marker (M13-K07 'phage'), and a 'phagemid' vector that includes only the F1 packaging region and minor coat protein-encoding gene from the virus. The former vector when introduced into a suitable bacterial host such as *E. coli* and propagated appropriately, will generate virus particles that display five copies of the chosen carbohydrate-binding domain at one end of the filamentous virus particle, as N-terminal fusions of the minor coat protein P3 (encoded by gene III).

The latter, due to the nature of virus propagation when using a phagemid/helper phage system, and familiar to those practiced in the art, will generate virus particles in which only a small minority of the population will display typically one or less copies of the same carbohydrate-binding domain-P3 fusion protein.

Clones derived from each vector were propagated under appropriate conditions, well known to those familiar with the technology, and the culture supernatants containing virus particles were screened by ELISA for binding activity to the major carbohydrate recognised by the carbohydrate-binding domain. In this example a complex molecule that includes a distal galactose group, and which is amenable to immobilisation by adsorption onto a typical 96 well immunoassay plate was used. In order to bind to the carbohydrate group, it is necessary for two or more of the carbohydrate-binding domains to associate in a complex as a carbohydrate binding pocket is formed between adjacent domains.

In the former 'phage' example, this could potentially be formed between adjacent P3 fusion proteins on a single virion, subject to acceptable orientation constraints of the fusion protein, or between separate virus particles. Using the phagemid system, such associations would most likely form between two or more separate virus particles as the proportion of viruses including two or more fusion proteins on a single virion is anticipated to be very small.

Upon screening the aforementioned clones, a significantly stronger ELISA signal was generated from the 'monovalent' phagemid-derived clone than from the penta-valent phage clone, the latter also producing a much lower titre of infective virus particles. The poor performance of the phage system in this example does not limit the utility of the system in the process described, but more likely is believed to be a function of either steric/orientation constraints imposed on the system by the particular genetic linkage employed here, and/or infectivity restrictions imposed by the fusion protein (the P3 minor coat protein is the mediator of virus infection). It was therefore the phagemid based system that was chosen to generate and select variant mutant proteins.

Example 2

Generation of Mutant Clone Libraries

Libraries of mutant polypeptide-encoding clones were generated from a genetic template derived from a carbohydrate-binding self-assembling protein domain. In the present example, the protein domain was selected from the A1B5 group of bacterial holotoxins. Structural and functional information obtained from published data bases such as the Protein Data Base, and the scientific literature, were used to identify regions and/or specific residues thought potentially or proven to be involved in the ability of the template protein domain to form stable homo-pentamers, or to interact with specific carbohydrate-containing moieties found on the surface of many mammalian cell types. These regions/residues were excluded from subsequent mutagenesis and mutant screening rounds.

Regions or residues defined as above as being potentially amenable to mutation and not involved in desired characteristics were selected and targeted for rational or random mutagenesis, as deemed appropriate. In order to maximise the chances of generating and selecting carbohydrate-binding variants that were divergent from the template domain, mutations were restricted to a limited number of residues in close proximity for each sequential round of library construction screening.

Depending on the region or residue being targeted, mutation was either random (i.e. including potentially all 20 amino acids), or functionally restricted as far as reasonably possible to those residues that display similar bio-physical and/or chemical properties to those found in the template domain.

Characteristics that were considered relevant in such cases included, but were not limited to, side chain size, charge, polarity, hydrophobicity/hydrophilicity, and the ability to participate in formation of specific secondary structures such as α-helices. Where possible/feasible, the residue encoded by the template in any given position was omitted from the mutant libraries to avoid selection of non-mutants.

Libraries were generated by designing oligonucleotide primers that included both regions of sequence that were homologous to the template gene such that the primer (and specifically its 3'-end) would anneal to the template DNA under appropriate conditions, and further regions in which appropriate degeneracy was included such as to encode a diversity of amino acids in one or more positions.

In the instant example, such oligonucleotides were constructed using defined degeneracy familiar to those instructed in the art whereby the DNA base in any diversified position comprised equal quantities of 2-4 bases (G, A, T or C) as required. Alternatively, more controlled diversity is envisaged whereby oligonucleotides generated from positional mixes of tri-nucleotide phosphoramidites are used such that the specific residues (amino acids) and their relative proportions are precisely controlled at each diversified position.

Where mutations were to be introduced at either terminus, a single PCR reaction was performed (and repeated when necessary) using one or two degenerate primers in order to introduce the required genetic diversity. The resulting product, which included (primer-derived) flanking restriction sites, was cloned into the phagemid vector outlined in example 1 above such that a library of variant proteins was encoded as in-frame genetic fusions to the minor P3 protein-encoding gene (gene III) of the M13 bacteriophage.

Where is was desired to introduce diversity into region(s) distal to the termini of the template gene, two pairs of primers were used such that each pair included one terminal (5' or 3') primer that exactly matched the template sequence, and one degenerate primer that encoded some, all or none of the required diversity. The 3'-end of the degenerate primers were designed such that i) each exactly matched the template sequence, and ii) each was exactly complementary to the degenerate primer from the second primer pair.

In this way, two PCR products were generated, and then annealed to and linked to each other via the complementary overlapping sequence derived from the degenerate primers. The resulting product was subsequently cloned into the phagemid vector as an in-frame genetic fusion with the gene III minor coat protein gene. Successive libraries were either built upon the outputs from screening and selecting one or more clones from the previous library, or were built and screened in parallel from the template or one or more selected mutant clones.

All genetic construct libraries were introduced into host *E. coli* TG1 cells by electroporation using standard methodologies, and transformants plated onto selective media. Following appropriate incubation, colonies of bacteria were scraped off plates and stored and/or screened as required.

Example 3

Screening of Mutant Libraries

In order to carry out selections of mutants from the libraries, cultures (of libraries) were inoculated into liquid media (2×TY, 100 µg/ml ampicillin, 1% glucose) such that sufficient cells to include 100-1000 fold representation of the anticipated diversity were included, and sufficient volume to ensure that the $OD_{600}$ was in the region of 0.1. Cultures were then incubated (with shaking) at about 37° C. until the $OD_{600}$ reached 0.4-0.6 (i.e. log phase growth). The cultures were then infected by the addition of M13 KO7 helper phage at the ratio of ~20 helper phage per bacterial cell ($OD_{600}$ of 1.0 taken to be ~8.0×10$^8$ cells/ml). After approximately 30 min static incubation, cells were incubated for about 30 additional min with shaking. Kanamycin was added to ~50 µg/ml and the cultured incubated overnight at ~30° C. with shaking.

The following morning, cultures were centrifuged for about 25-30 min at ~8,000 g to pellet cells, and the supernatant removed and retained. Cell pellets were discarded. A 20% volume of 200 mM NaCl, 20% PEG 6,000 was added to the culture supernatant, and incubated on ice for about 1 h to precipitate phage particles. Phage were pelleted at 8,000 g for about 25-30 min., and re-suspended in 20 percent of the original volume PBS (phosphate-buffered saline). Again, 20% new volume of 200 mM NaCl, 20% PEG 6,000 was added and the phage incubated on ice for about 25-30 min. The phage were pelleted again at ~8000 g for 25-30 min, and the pellet re-suspended in ~2 ml phosphate buffered saline (PBS). The resulting suspension was transferred to Eppendorf tube(s) and pelleted at maximum speed for 5 min to pellet any remaining bacterial cells/debris. The phage suspension was then used for selections.

In order to carry out selections, an immunotube was coated with a suitable antigen such as an immobilizable derivative of galactose, or a natural ligand of the B-subunit, at 1-10 µg/ml (typically 5 ml) overnight at 4-8° C. or at room temperature for 1 h. After washing 3-5 times with PBS (by simply pouring into the immunotube and pouring out again), the tube was blocked by the addition of MPBS (PBS containing 2% milk powder) for 1-2 h at 37° C. The MPBS was washed out as described above, and approximately 1×10$^{11}$ to 1×10$^{12}$ or more phage particles added.

The volume was made up to ~5 ml, and the immunotube sealed e.g. with para-film. It was then 'tumbled' (end-over-end) for about 30 min, then incubated standing for about 90 min to allow those phage that display a protein from the mutant library that is able to recognise the immobilised ligand, to bind to it. Phage that had not bound, or were only weakly bound, were removed by washing. The stringency of the selection was varied as required by the number of washes used, the use of PBST (PBS containing 0.1% Tween 20) to wash, or adjusting the coating concentration of ligand.

Bound phage particles were eluted from the immunotube by adding 1 ml 100 mM triethylamine (TEA) and tumbling for a maximum of 10 min (longer incubation adversely affects phage viability), then pouring immediately into 0.5 ml 1 M Tris-HCl (pH 7.4) to neutralise. About 0.75 ml eluted phage was added to ~10 ml log phase culture of a suitable E. coli strain such as TG1 (Agilent). The culture was incubated at about 37° C. without shaking to allow infection. Serial dilutions of a sample of the infected cells were spread onto small TYE plates containing 100 µg/ml ampicillin and 1% glucose. The remaining cells were plated onto larger bioassay plates with the same media. All were incubated overnight at about 30° C. Of the other 0.75 ml phage, ~75 µl were infected as above into ~1 ml log phase E. coli HB2151 cells and serial dilutions plated out as and incubated as above. The remaining phage were stored at about −80° C. as a glycerol stock (~15% glycerol).

The following day large bio-assay plates were scraped to remove the cells, which were then stored as glycerol stocks or grown and 'rescued' with M13 KO7 helper phage as described earlier, to prepare an enriched population of phage for the next round of selection. Typically two to three sequential rounds of selection were carried out. Upon completion of selections, individual colonies from the small serial dilution plates of HB2151 cells were picked into 96 well culture plates containing 100 µl/well 2×TY with 100 µg/ml ampicillin, and incubated with shaking overnight at 37° C. The following day, approximately 5 µl culture from each well was inoculated into a fresh plate with ~150 µl media/well, and incubated at about 37° C. with shaking for about 2 hours. Additional media containing 1 M IPTG was added to give a final concentration of 1 mM IPTG, and the plate incubated with shaking overnight at 30° C. In HB2151 cells, induction with IPTG results in the expression of soluble mutant proteins including a detectable c-myc peptide tag, rather than proteins fused to a component of a virus particle as is the case with E. coli TG1 cells. The initial 96 well culture plate was stored at about −80° C.

The next day, culture supernatants from the induced 96 well plate were assayed for binding to immobilised carbohydrate using typical ELISA protocols, and binding detected with a readily available HRP-labelled anti-c-Myc antibody (FIG. 1). Clones that were strongly positive for binding to GM1 are shown in shaded cells. Positive and negative controls are boxed.

Culture supernatants from clones that were strongly positive by binding ELISA were further analysed by SDS PAGE and Western blot to assess the presence of pentamers and other multimeric states as illustrated in FIG. 2. Samples were not reduced or boiled prior to electrophoresis, and protein was detected with HRP-labelled anti-c-Myc antibody. In the example shown, clones C1 and C3 are positive controls that readily assemble into pentamers of ~60 kDa. Clone C2 is a negative control that runs as a 12 kDa monomer under the conditions used. Clones A1 and A3 can be seen to run primarily as pentamers, whereas a significant proportion of clone B12 forms monomers. The remaining clones form either only monomer (B1, B7) or form many multimeric forms.

Example 4

Compilation of Mutations

Figure 3:
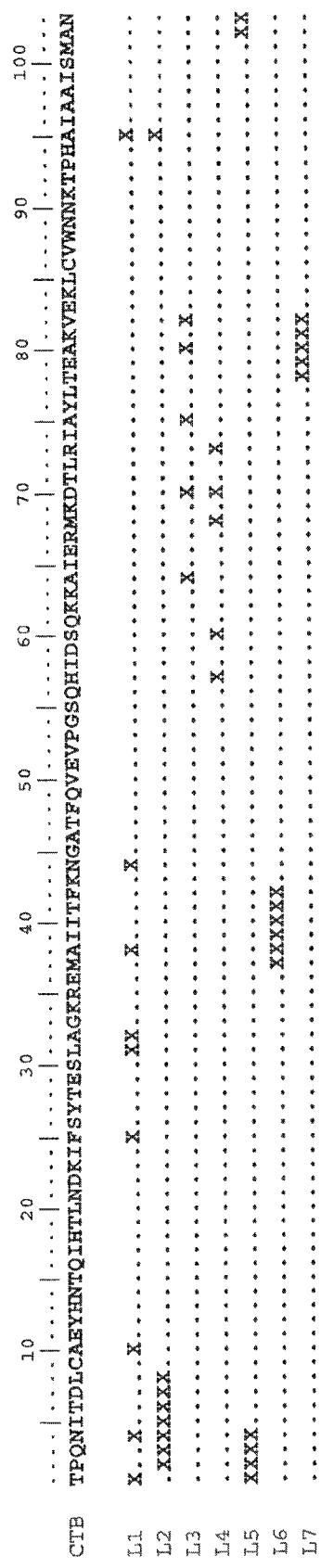
FIGS. 3A and 3B. Illustrate a selection of mutations identified after selecting and screening several mutant libraries FIG. 3(a) Sequences of a selection of mutants, each isolated from one of 7 separate mutant libraries and illustrating the distribution of mutated residues relative to wild-type CTB (SEQ ID NO: 18), and FIG. 3(b) sequences of synthetic proteins derived from compiling mutations derived from several different mutant clones.
Figure 4:
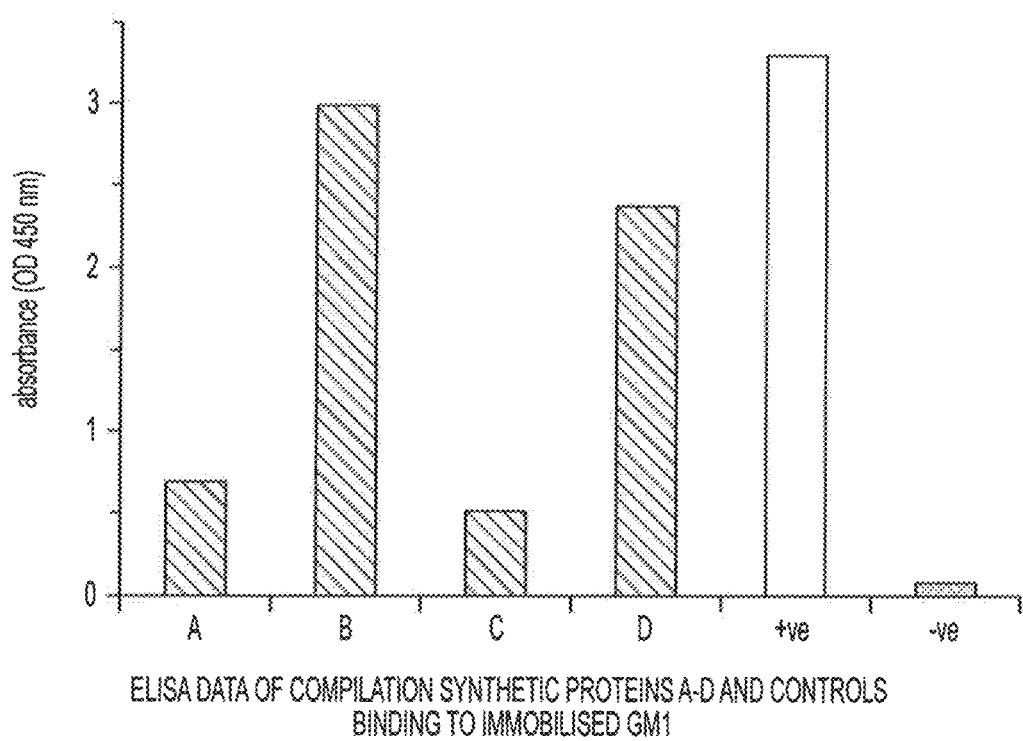
FIG. 4. Illustrates GM1-binding ELISA data from four compilation mutants, showing that two clones have retained galactose binding activity, and two have not.

In order to assess the capacity of the maximum number of residues to accommodate mutations, several different libraries each targeting different residues or regions of the template, were constructed and screened. As a result, a large number of clones were identified that exhibited the desired selection criteria of binding to immobilised carbohydrate derivatives and of forming predominantly pentamers, however each of which included a number of unique mutations/differences relative to wildtype CTB (SEQ ID NO: 18) as illustrated in FIG. 3A. In order to generate clones with potentially enhanced characteristics it was necessary to combine these varied sequences into a smaller number of clones.

As the mutant generation and selection process had identified several positions where three or more different residues could be accommodated, a total of four combination mutants (A-D) were designed as illustrated in FIG. 3B. The four clones containing combined mutations were expressed, and the synthetic proteins evaluated for their binding compared to appropriate controls by ELISA as illustrated in FIG.

4. It was found that two of the clones (A and C) had only weak binding, however the other two (B and D) were able to bind to GM1 very strongly. This indicates that mutations derived from separate clones can be combined successfully, however the enhancement or even retention or of selected binding characteristics is not guaranteed.

Example 5

Stabilization of Homo-Pentamers

Figure 5:
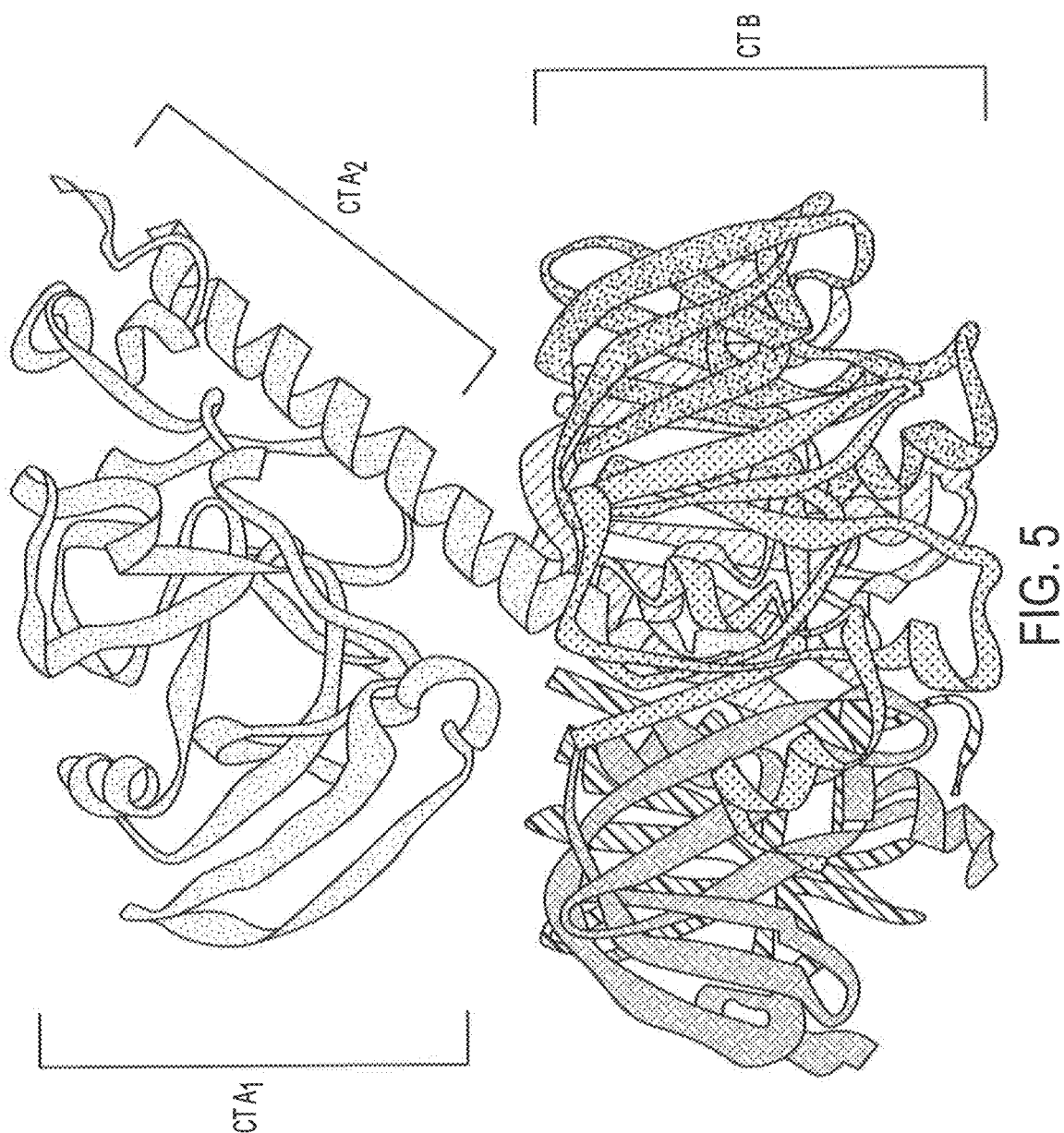
FIG. 5. Illustrates the structure of the complete cholera holotoxin molecule.

In their native fully functional form, the bacterial holo-toxins described by the group name 'A1B5' comprise five B-subunits and a single A-subunit. The B subunits assemble into a pentameric ring with a central 'pore'. A single A-subunit sits atop this ring and projects down into the void as illustrated in FIG. 5. The A-subunit itself comprises 2 distinct domains. The A1 domain, which is released when the holotoxin is translocated into a cell, contains the enzymatic activity associated with the toxicity of the protein complex. It is held as a part of the holotoxin by the A2 domain. This has an alpha-helical structure in which the A1 domain sits at the N-terminus, and the C-terminus projects into the pore formed by the 5 B-subunits. Some residues of the C-terminus of A2 form interactions with residues of the B-subunits. As there are confirmed interactions between specific residues of the B-subunits and the A2 domain (Zhang R. G., et al (1995)), it is reasonable to suggest that the presence of the A-subunit, and specifically the A2 domain, contributes to stabilizing the pentameric B-subunit ring. Due to the structural and functional distinctions between the two A-subunit domains, without being bound to any particular theory, it is thought that the A2 domain alone would confer this stabilizing effect on a B-subunit pentamer. Similarly, as it is known that B-subunits are able to form pentameric rings in the complete absence of the A-subunit, it is probable that the A2 domain could associate with, and therefore exert a stabilizing effect on B-subunit pentamers by either being co-expressed with the B-subunits, or by being added exogenously.

It is therefore proposed that a synthetic or non-naturally occurring polypeptide, that shares a sufficiently similar conformation to holotoxin B-subunits, that is able to assemble into multimers including pentameric rings, and in which the residues corresponding to those that interact with A2 in holotoxin B-subunits are the same or share the same bio-physical properties, then such a synthetic protein pentamer would experience a similar stabilizing benefit. Moreover, it is suggested that in the absence of a natural A2 domain, a synthetic polypeptide could be isolated from a suitable polypeptide library using technologies familiar to those practiced in the art such as 'phage display', that would bind at least in part to the exposed surfaces of two or more natural or synthetic monomers when assembled into a pentamer, and so stabilize the structure.

As naturally occurring A2 domains support a structurally independent A1 domain that does not in itself interact with any other component of the holotoxin, then it is probable that an A2 domain or a functional synthetic equivalent could provide a means of anchoring another polypeptide domain. Without being bound to any particular theory, it is thought that non-naturally occurring polypeptide, that shares a sufficiently similar conformation to polypeptide described in SEQ ID NO: 1 contributes by itself to form pentameric rings exhibiting a stabilized pentameric ring structure allowing for the attachment of epitopes as described within this disclosure.

Example 6

Figure 7:
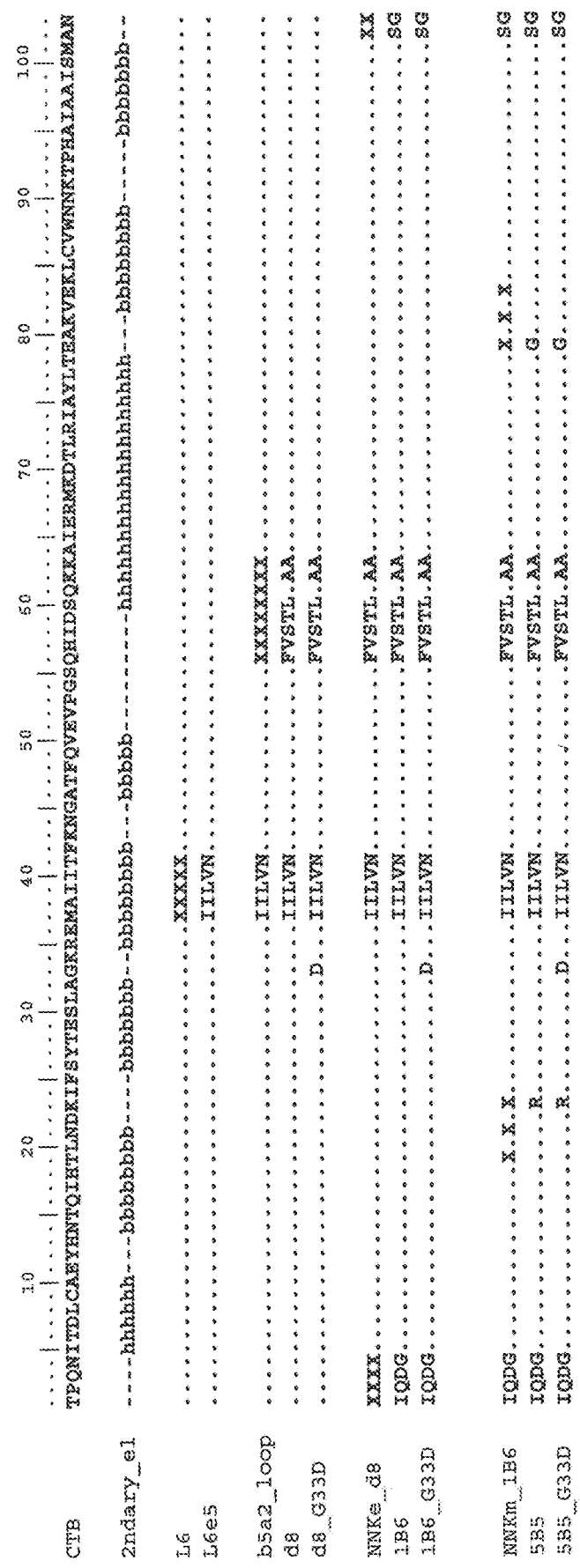
FIG. 7. Illustrates the distribution of targeted residues in several mutant libraries (a), and sequences of synthetic proteins (templates) successively obtained (b)
Figure 8A:
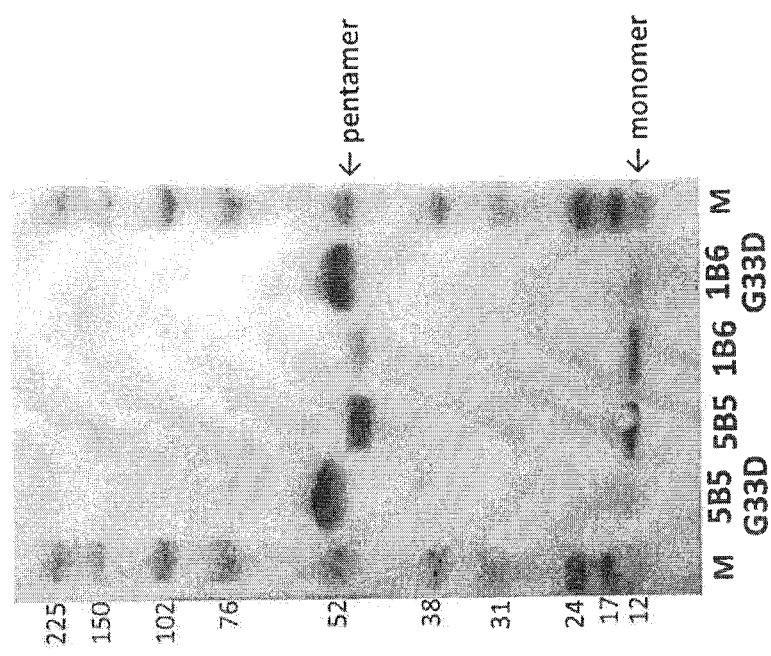
FIGS. 8A and 8 Illustrate GM1-binding ELISA (a) and Western blot (b) of synthetic carrier (SEQ ID NO: 3, 5B5 −/+G33D) and its immediate precursor (1B6). Specific detection was via cMyc-tag.
Figure 8B:
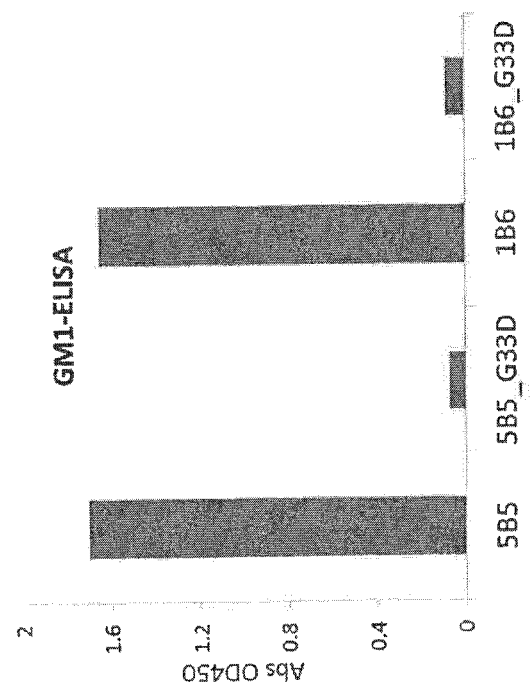

Reference is to FIG. 7 for subsequent mutation events. A major binder from the screening that targeted mutations (library 6) in a confined region (the β3 strand) of CTB was selected. Starting off with this template (L6e5) one mutagenesis intermezzo without library construction and screening was carried out. It involved the same DNA methodology as forth in EXAMPLE 2, i.e. generation of PCR products and subsequent annealing/linking via complementary overlapping sequence. The (β5-α2) loop (positions 55-64), a 'permissive' site proposed by Backstrom et al. (Gene, 1994), was addressed for inserting peptides. Some non-human epitope peptides were tested and substitution with FVSTLQAA passed criteria (GM1 binding and pentamer formation). The DNA sequence of this carrier was the template for generating the next library, targeting the flexible ends of the protein (positions 1-4 and 102-3). Screening did deliver mutants meeting criteria and the DNA sequence of one of them was used as template in a library targeting two untouched middle regions (approximate β1-β2 and α2-β5 loops). Once more did screening release GM1-binding pentameric proteins. One of them is notable (5B5, 20% changed u CTB), (FIGS. 8A and 8B, SEQ ID NO: 3).

Figure 9A:
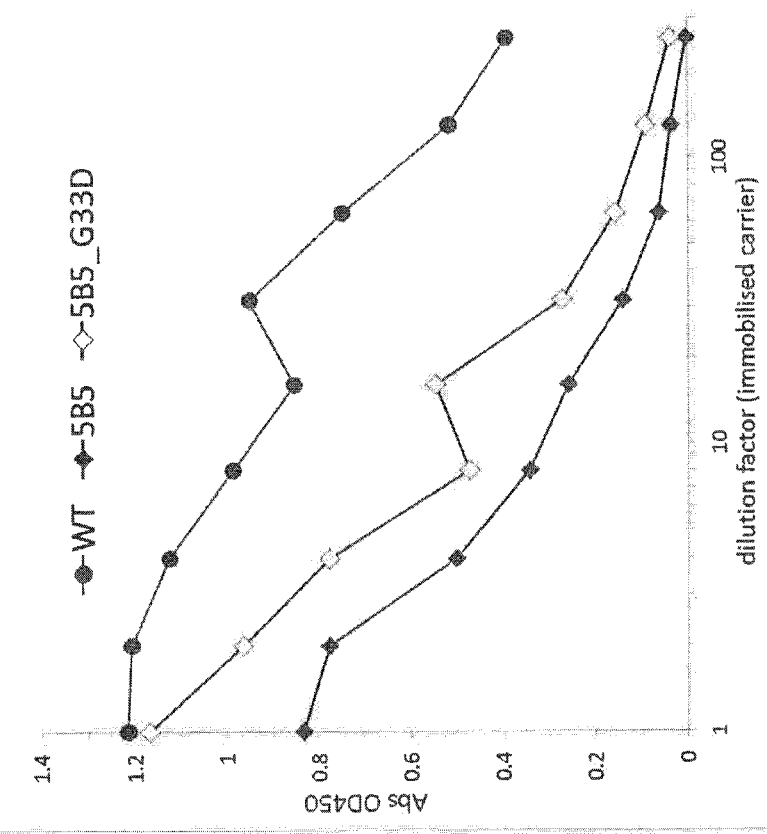
FIGS. 9A and 9B. Illustrate impaired detection of synthetic carrier by anti-CTB monoclonal antibody (a) and polyclonal anti-CTB serum (b)
Figure 9B:
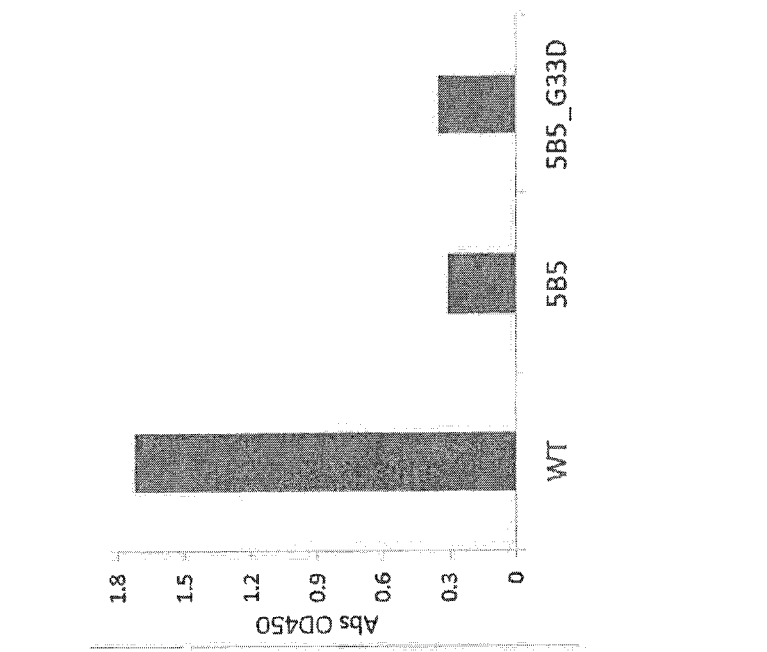

Synthetic carrier 5B5 was assessed in ELISAs with anti-CTB antibodies. Detection by a monoclonal was significantly impaired (FIG. 9A). Polyclonal antibodies (three suppliers tested) exhibited a trend towards reduced detection of 5B5. This is illustrated for one of them (a sheep serum source) with normalised amounts of carrier (FIG. 9B).

In addition, we propose the practicality of the glycine (G) to aspartate (D) mutation at position 33 of the carrier/subunit sequence (Jobling & Holmes, Mol. Microbiol. 1991). The G33D mutation disables ganglioside GM1 binding but subunits still form a pentamer. This was confirmed for binders selected for next mutation round (FIG. 7), but its G33D DNA version was obviously not used as next-round template, and the final 5B5 (FIGS. 7 and 8: the introduced negatively charged aspartate gives it a slower electrophoretic mobility). GM1 is present on all cells. A synthetic carrier that is not able to bind GM1 will be available/presented to immune cells in a higher dosage. Moreover, GM1-binding inability, 20% sequence difference, impaired detection with anti-CTB antibodies, and (pending, see below) absence of assembly with CTA makes it distinct from CTB.

Figure 10:
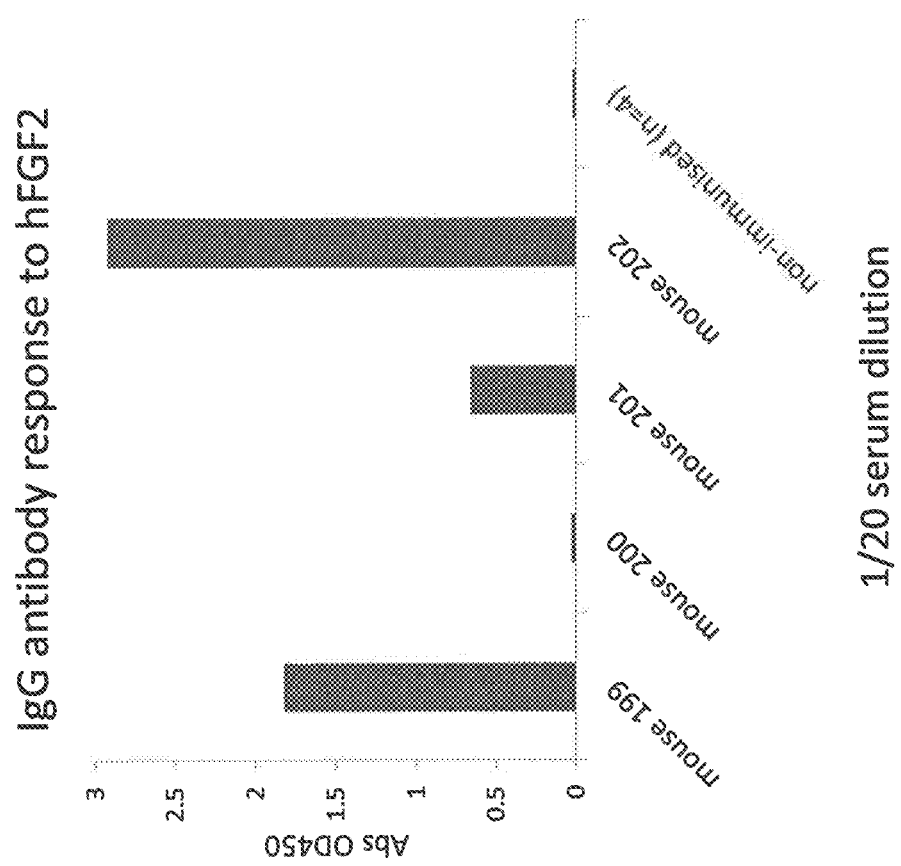
FIG. 10. Illustrates immunogenicity of synthetic carrier (precursor) fused to hFGF2. Depicted are IgG responses to hFGf2, in mice sera 28 days after immunisation.

During processing of the last two libraries, precursor carrier d8_G33D (12% substituted) was fused to a growth factor, this time hFGF2, and His6-tag purified recombinant conjugate was used to immunize mice, via i.m. administration. Significant IgG antibody responses against FGF2 were obtained (FIG. 10). Immunizations of 5B5 and follow-ups, with and without G33D, fused to hFGF2 (SEQ ID NO: 4) are planned (pending purification and characterization).

Example 7

Figure 11B:
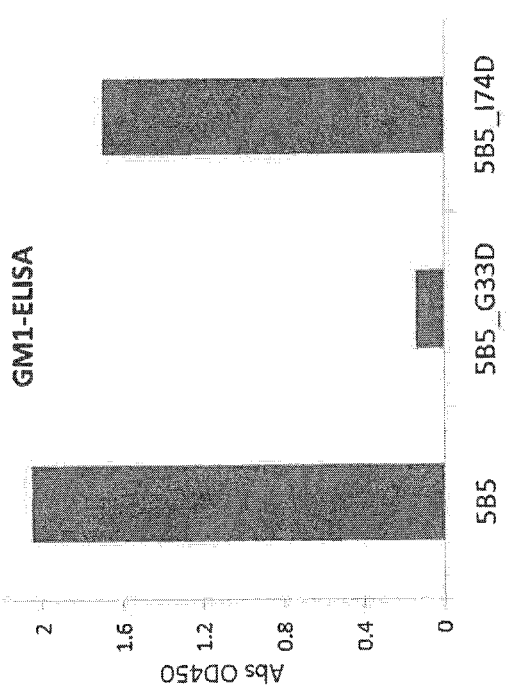
FIGS. 11A and 11B. Illustrate GM1-binding ELISA (a) and culture medium and crude periplasm preps signals on Western blot (b) of carrier 5B5_I74D, potentially deficient in assembling with CTA2. Including 5B5, 5B5_G33D and 5B5_T78D.
Figure 11A:
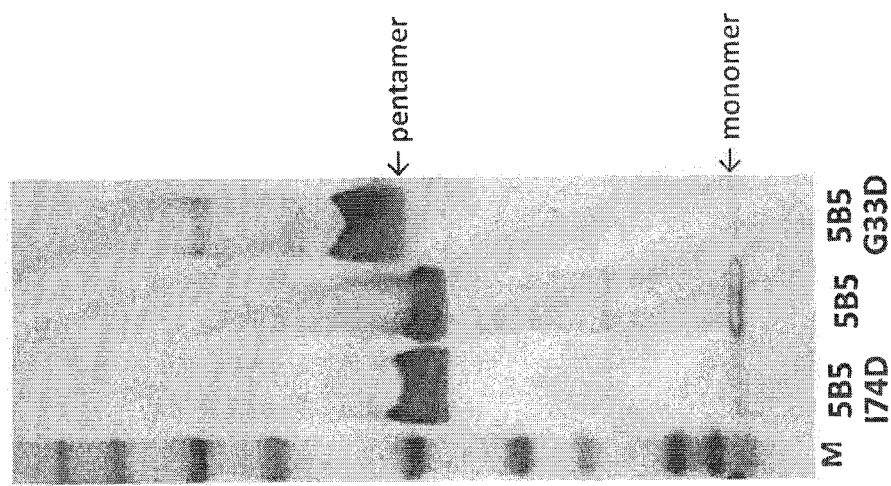

The cholera holotoxin is an AB5 hexamer, i.e. CTA non-covalently interacts with the CTB pentamer, entering cells via ganglioside GM1 cell surface receptor. The proposed synthetic carrier pentamer is distinct form CTB, besides at least 20% sequence difference and its inability to bind GM1, if it does not bind (the CTA2 component) of CTA. Tinker et al. (Infect. Immun. 2003) have shown that substituting a single residue in CTB (I74D or T78D, in the region interacting with CTA2) disables holotoxin assembly. Synthetic carrier 5B5 with these single mutations still formed pentamers, as shown in FIGS. 11A and 11B for I74D, but absence of interaction with CTA2 in vitro has not been established yet.

Example 8

It is anticipated that a monomeric carrier will be useful to fuse to and purify complicated antigens, like dimeric TGFβ1 growth factor. With the latter it will still be exposed to the immune cells/system as a relatively large (four entities) complex. Modelling of CTB has revealed exposed hydrophobic residues potentially involved in subunit interaction/multimerisation. By changing them to hydrophilic/polar amino acids (e.g. F25R, L31E, A32Q, L77N) the current pentameric synthetic carrier (5B5), may well be converted to a monomeric version.

Although the devices, systems, and methods have been described and illustrated in connection with certain embodiments, many variations and modifications will be evident to those skilled in the art and may be made without departing from the spirit and scope of the disclosure. The discourse is thus not to be limited to the precise details of methodology or construction set forth above as such variations and modification are intended to be included within the scope of the disclosure.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

---

What is claimed is:

1. A recombinant synthetic protein, comprising:
a monomeric polypeptide sequence able to assemble into stable homo-pentamers, wherein the monomeric polypeptide sequence includes
a synthetic β subunit of an A1B5 group of bacterial holotoxins derived from a Cholera Toxin B (CTB) subunit that includes at least one mutation relative to a wildtype CTB amino acid sequence (SEQ ID NO: 18) selected from the group consisting of T1F, P2T, Q3D, N4I, M37I, A38I, I39L, I40V, T41N, T78S, E79N, A80S, A95S, A102V, and N103R,
a peptide spacer, and
a polypeptide including a full length Epidermal Growth Factor (EGF),
wherein the polypeptide is separated from the synthetic β subunit by the peptide spacer.

2. The recombinant protein according to claim 1, wherein the synthetic β subunit of an A1B5 group of bacterial holotoxins is SEQ ID NO: 18.

3. The recombinant protein according to claim 1, wherein the at least one mutation relative to a wildtype CTB amino acid sequence (SEQ ID NO: 18) further includes a mutation selected from the group consisting of L8I, A10G, F25L, A32V, N44G, V82I, A95S, and combinations thereof.

4. The recombinant protein according to claim 1, wherein the synthetic β subunit is IQDGITDLCAEYHNTQIHTLN-DRIFSYTESLAGKREBLVNFKNGATFQVEVPGS-FVSTLQ AAAIERMKDTLRIAYLTGAKVEKLCVWNN-KTPHAIAAISMSG (SEQ ID NO: 3).

5. The recombinant protein according to claim 1, wherein the polypeptide further includes a full length of a second growth factor selected from the group consisting of IGF-1, IGF-2, FGF1, FGF2, TGF-α, TGF-β, VEGF-A, VEGF-B, VEGF-C, VEGF-D, PDGF, NGF, EGF, HGF, BMP's, PDL1 and IL's 1-6.

6. The recombinant protein according to claim 1, wherein the polypeptide includes a full length of one or more growth factors as a single domain or as two or more multiple repeats.

7. The recombinant protein according to claim 1, wherein the polypeptide spacer is selected from the group consisting of SSG (SEQ ID NO:5), SSGGG (SEQ ID NO:6), SGG (SEQ ID NO:7), GGSGG (SEQ ID NO:8), GGGGS (SEQ ID NO:9), SSGGGSGGSSG (SEQ ID NO:10), GGSGGTSGGGSG (SEQ ID NO:11), SGGTSGGGGSGG (SEQ ID NO:12), GGSGGTSGGGGSGG (SEQ ID NO:13), SSGGGSGGSSG (SEQ ID NO:14), SSGGGGSGGGSSG (SEQ ID NO:15), SSGGGSGGSSGGG (SEQ ID NO:16), and SSGGGGSGGGSSGGG (SEQ ID NO:17).

8. The recombinant protein according to claim 1, wherein the polypeptide spacer includes an amino acid sequence of a growth factor.

9. The recombinant protein according to claim 1, wherein the polypeptide spacer includes one or more host T-cell epitopes.

* * * * *